(12) United States Patent
Parent et al.

(10) Patent No.: US 8,927,761 B2
(45) Date of Patent: Jan. 6, 2015

(54) FORM OF HEXYL-5-AMINOLEVULINATE HYDROCHLORIDE AND METHODS OF USING THE SAME

(71) Applicants: Stephan D. Parent, West Lafayette, IN (US); Jon Erik Brænden, Oslo (NO)

(72) Inventors: Stephan D. Parent, West Lafayette, IN (US); Jon Erik Brænden, Oslo (NO)

(73) Assignee: Photocure ASA, Oslo (NO)

( * ) Notice: Subject to any disclaimer, the term of this patent is extended or adjusted under 35 U.S.C. 154(b) by 0 days.

(21) Appl. No.: 13/930,497

(22) Filed: Jun. 28, 2013

(65) Prior Publication Data

US 2014/0010761 A1    Jan. 9, 2014

Related U.S. Application Data

(60) Provisional application No. 61/665,654, filed on Jun. 28, 2012.

(51) Int. Cl.
*C07C 229/22* (2006.01)
*A61K 49/00* (2006.01)
*A61K 41/00* (2006.01)

(52) U.S. Cl.
CPC ........... *C07C 229/22* (2013.01); *A61K 49/0052* (2013.01); *A61K 41/0061* (2013.01)
USPC .......................................... 560/170; 514/551

(58) Field of Classification Search
CPC .. C07C 229/22; C07C 229/16; C07C 227/16; C07C 69/67
See application file for complete search history.

(56) References Cited

PUBLICATIONS

Dabrowski et al. Acta Poloniae Pharmaceutica-Drug Research 2003, 60, 3, 185-193.*
Lange et al. British Journal of Cancer (1999) 80(1/2), 185-193.*

* cited by examiner

*Primary Examiner* — Brandon Fetterolf
*Assistant Examiner* — Ana Z Muresan
(74) *Attorney, Agent, or Firm* — Kenyon & Kenyon LLP

(57) ABSTRACT

This invention relates to a novel crystalline polymorph of hexyl-5-aminolevulinate hydrochloride, referred to hereinafter as Form C, which is useful as precursor of a photo sensitizer in the photodynamic diagnosis and treatment of metabolically active cells related to diseases such as cancer of the uterus, cervix, vagina, rectum, colon, lower gastrointestinal tract; infection associated with cancer caused by human papilloma virus; non-cancerous lower gastrointestinal tract a human; inflammatory bowel disease; ulcerative colitis; Crohn's disease; inflammatory bowel syndrome; dysplasia of the female reproductive system; anus; penis; rosacea; and acne and which is suitable for use as the active ingredient of a commercial pharmaceutical product. The invention relates further to methods of preparing Form C and using it in the described pharmaceutical compositions.

25 Claims, 11 Drawing Sheets

Temp = 25.9 °C, Initial Material

Temp = 68.1 °C, ~3 Minutes, Changes in Birefringence and Lath Formation

Temp = 68.1 °C, ~6 Minutes

Temp = 68.1 °C, ~20 Minutes, Increased Lath Formation

Temp = 92.3 °C, Continuation of Lath Formation and Changes in Birefringence

_US 8,927,761 B2_

FORM OF HEXYL-5-AMINOLEVULINATE HYDROCHLORIDE AND METHODS OF USING THE SAME

RELATED APPLICATIONS

This claims the benefit of U.S. Provisional Application No. 61/665,654, filed on Jul. 28, 2013.

BACKGROUND

Photodynamic diagnosis (PDD) is a technique for the identification of metabolically active cells. Examples of metabolically active cells are cells which undergo an abnormal growth pattern. Such abnormal growth patterns include an increased number of cells/increased cell proliferation (hyperplasia), abnormal maturation and differentiation of cells (dysplasia) and abnormal proliferation of cells (neoplasia). The cells of a hyperplastic growth remain subject to normal regulatory control mechanisms. Cells of a neoplastic growth are genetically abnormal cells which proliferate in a non-physiological manner which is unresponsive to normal stimuli. Other examples of metabolically active cells are inflamed cells or infected cells. Hence PDD can be used for the diagnosis of pre-cancerous lesions, cancer and non-cancerous diseases.

PDD involves the administration of a photosensitizer or a precursor thereof to an area of interest. The photosensitizer or precursor thereof is taken up into the cells, where a precursor of a photosensitizer is converted into a photosensitizer. Upon exposure of the area of interest to light, the photosensitizer is excited and displays in response a fluorescence which is detected. The photosensitizer accumulates preferentially in metabolically active cells and tissue, such as inflamed or neoplastic tissue; hence such tissue can be distinguished from healthy tissue. Studies suggest that accumulation is not due to selective uptake by metabolically active, e.g. cancerous cells, rather, there are similar levels of uptake in all cell types, but the processes of conversion and elimination are different in metabolically active cells, such as neoplastic tissue, leading to a concentration gradient of photosensitizer between e.g. inflamed/neoplastic and normal tissue.

Several photosensitizers and precursors thereof are known and described in the literature, including 5-aminolevulinic acid (5-ALA) and certain derivatives thereof, e.g. 5-ALA esters, both of which are precursors of photosensitizers. These are converted intracellularly to protoporphyrins, such as protoporphyrin IX (PpIX), which are photosensitizers. Currently several pharmaceutical products comprising 5-ALA or an ester thereof are in clinical use for (PDD) but also for photodynamic therapy (PDT). One of them is Metvix®, a dermal product in the form of a cream comprising the hydrochloride salt of methyl 5-ALA ester (i.e. methyl-5-aminoveluvinate hydrochloride), developed by Photocure ASA, Norway, and now sold by Galderma, Switzerland, for the photodynamic therapy of actinic keratosis and basal cell carcinoma. Another one is Levulan Kerastick® (DUSA Pharmaceuticals, Canada), a product for the photodynamic therapy of actinic keratosis which contains the hydrochloride salt of 5-ALA. Hexvix® (Photocure ASA) is an aqueous solution which comprises the hydrochloride salt of hexyl 5-ALA, i.e. hexyl-5-aminolevulinate hydrochloride (HAL) for instillation into the bladder for diagnosis of bladder cancer.

There is an ongoing need to provide a convenient ready-to-use form of a PDD and/or PDT compound, e.g., that also allows the compositions to be prepared with a reliable and accurate concentration, which would be useful in the treatment and diagnosis of the majority of diseases, including cancer where it can be critical that the correct and efficient dosage of therapeutic or diagnostic is administered.

The present invention thus provides a novel crystalline polymorphic form of hexyl-5-aminolevulinate hydrochloride. Said novel crystalline polymorphic form of hexyl-5-aminolevulinate hydrochloride is useful in PDT and PDD.

Crystalline polymorph forms of a particular drug can be determinant of the drug's ease of preparation, stability, solubility, storage stability, ease of formulation and in vivo pharmacology. Polymorphic forms occur where the same composition of matter crystallizes in a different lattice arrangement resulting in different thermodynamic properties and stabilities specific to the particular polymorph form. Different polymorphs of a given compound may differ from each other with respect to one or more physical properties, such as solubility and dissociation, true density, crystal shape, compaction behavior, flow properties, and/or solid state stability.

SUMMARY

This invention relates to a novel crystalline polymorph of hexyl 5-aminolevulinate hydrochloride, referred to hereinafter as Form C, which is a precursor of a photosensitizer and thus useful in photodynamic diagnosis and treatment, e.g. in photodynamic diagnosis and treatment of metabolically active cells. Such cells may be cells which undergo an abnormal growth pattern. Such abnormal growth patterns include an increased number of cells/increased cell proliferation (hyperplasia), abnormal maturation and differentiation of cells (dysplasia) and abnormal proliferation of cells (neoplasia). Other examples of metabolically active cells are inflamed cells or infected cells, e.g. viral infection, bacterial infection or fungal infection.

Hence Form C is useful as a precursor of a photosensitizer (an active ingredient) in a commercial pharmaceutical product for use in photodynamic diagnosis and treatment of pre-cancerous lesions, cancer and non-cancerous diseases on internal and external body surfaces. Examples of such internal and external body surfaces include the skin and all other epithelial and serosal surfaces, including for example mucosa, the linings of organs e.g. the respiratory, gastro-intestinal and genito-urinary tracts, and glands with ducts which empty onto such surfaces (e.g. liver, hair follicles with sebaceous glands, mammary glands, salivary glands and seminal vesicles). In addition to the skin, such surfaces include for example the lining of the vagina, the endometrium and the urothelium. Such surfaces may also include cavities formed in the body following excision of diseased or cancerous tissue e.g. brain cavities following the excision of tumors such as gliomas. Exemplary surfaces thus include: (i) skin and conjunctiva; (ii) the lining of the mouth, pharynx, esophagus, stomach, intestines and intestinal appendages, rectum, and anal canal; (iii) the lining of the nasal passages, nasal sinuses, nasopharynx, trachea, bronchi, and bronchioles; (iv) the lining of the ureters, urinary bladder, and urethra; (v) the lining of the vulva, vagina, cervix, and uterus; (vi) the parietal and visceral pleura; (vii) the lining of the peritoneal and pelvic cavities, and the surface of the organs contained within those cavities; and (viii) the dura mater and meninges.

Form C is useful in the photodynamic diagnosis and treatment of pre-cancerous lesions, cancer and non-cancerous diseases of the uterus, cervix, vagina, rectum, colon, lower gastrointestinal tract such as infections associated with pre-cancer and cancer caused by human papilloma virus; non-cancerous diseases of the lower gastrointestinal tract such as inflammatory bowel disease; ulcerative colitis; Crohn's disease; inflammatory bowel syndrome; dysplasia of the female reproductive system; anus; penis; rosacea; and acne and which is suitable for use as the active ingredient of a commercial pharmaceutical product.

Form C exhibits a characteristic X-ray powder diffraction pattern with characteristic peaks expressed in degrees 2θ±0.20 at approximately 17.64, 19.29, 24.94, and 25.29. In other embodiments, Form C exhibits an X-ray powder diffraction pattern comprising characteristic peaks expressed in degrees 2θ±0.20 at approximately 2.96, 17.10, 17.64, 18.24, 19.29, 19.52, 20.11, 21.83, 24.94, and 25.29. In another embodiment, Form C exhibits an X-ray powder diffraction pattern comprising characteristic peaks expressed in degrees 2θ±0.20 at approximately 2.96, 9.08, 17.10, 17.64, 17.99, 18.24, 19.29, 19.52, 20.11, 21.83, 24.94, 25.29, 26.01 and 27.18. In another embodiment, Form C exhibits an X-ray powder diffraction pattern comprising characteristic peaks expressed in degrees 2θ±0.20 at 2.96, 5.95, 9.08, 11.65, 17.10, 17.64, 17.99, 18.24, 19.29, 19.52, 20.11, 21.30, 21.83, 22.73, 23.42, 24.94, 25.29, 26.01, 27.18, 27.51, 28.20 and 29.41. The X-ray powder diffraction pattern for Form C may be according to FIG. 1 or FIG. 2, or provided in Tables 1 or 2.

In some embodiments, Form C contains two or more X-ray power diffraction peaks, in terms of 2θ±0.20 at about 2.96, about 9.08, about 17.10, about 17.64, about 17.99, about 18.24, about 19.29, about 19.52, about 20.11, about 21.83, about 24.94, about 25.29, about 26.01 and about 27.18. In some embodiments, Form C contains two or more X-ray power diffraction peaks, in terms of 2θ±0.20, at about 2.96, about 5.95, about 9.08, about 11.65, about 17.10, about 17.64, about 17.99, about 18.24, about 19.29, about 19.52, about 20.11, about 21.30, about 21.83, about 22.73, about 23.42, about 24.94, about 25.29, about 26.01, about 27.18, about 27.51, about 28.20, and about 28.41.

In some embodiments, Form C contains or has an X-ray power diffraction substantially similar to FIG. 1 or FIG. 2. In some embodiments, Form C includes at least two X-ray power diffraction peaks in terms of 2θ±0.20 as shown in Table 1 or Table 2.

In some embodiments, Form C contains or has a DSC or TGA thermogram substantially similar to FIG. 3.

In some embodiments, Form C contains or has an infrared spectrum substantially similar to FIG. 5. In some embodiments, Form C contains at least two infrared spectrum peaks as shown in Table 3 or Table 4.

In some embodiments, Form C contains or has a Raman spectrum substantially similar to FIG. 6. In some embodiments, Form C contains at least two Raman spectrum peaks as shown in Table 5 or Table 6.

In some embodiments, Form C contains or has a solid-state carbon NMR spectrum substantially similar to any one of FIGS. 7-9. In some embodiments, Form C contains at least two chemical shifts for solid-state carbon NMR as shown in Table 7.

In some embodiments, the hexyl-5-aminolevulinate hydrochloride contains less than 5% by weight impurities. In some embodiments, the hexyl-5-aminolevulinate hydrochloride is at least 50% pure, at least 75% pure, at least 80% pure, at least 90% pure, at least 95% pure, or at least 98% pure.

Embodiments also relate to a pharmaceutical composition comprising Form C, and a pharmaceutically acceptable carrier. In some embodiments, the pharmaceutical composition further includes one or more of at least one triglyceride, at least one emulsifier, one or more mucoadhesives, one or more pharmaceutically acceptable excipients, one or more surface penetration agents; or one or more chelating agents.

In some embodiments, the pharmaceutical composition contains a solid, a suppository, a pessary, a solution, an elixir, a suspension, an emulsion, a syrup, an aerosol, a sterile injectable solution, a sterile packaged powder, a cream, an ointment, or a lotion. In some embodiments, the pharmaceutical composition is substantially water-free.

In some embodiments, the pharmaceutical composition is a solid capsule. In some embodiments, the solid capsule is coated with at least one enteric coating. In some embodiments, the at least one enteric coating allows for the pH controlled release of the Form C in the range of a pH of about 5.5 to a pH of about 7.5. In some embodiments, the at least one enteric coating is selected from the group of: Eudragit® S100, Eudragit® L100, TEC and talc.

In some embodiments, the pharmaceutical composition includes at least one selected from the group of: an agar, an alginic acid, ascorbic acid, an amino acid, citric acid, a calcium salt, an ammonium salt.

In some embodiments, the pharmaceutical composition includes at least one triglyceride.

In some embodiments, the pharmaceutical composition includes at least one mucoadhesive agent.

In some embodiments, the pharmaceutical composition includes at least one surface penetration agent.

In some embodiments, the pharmaceutical composition includes at least one chelating agent.

In some embodiments, the pharmaceutical composition further includes a buffering agent.

In some embodiments, the pharmaceutical composition further includes a cryoprotective agent.

In some embodiments, the pharmaceutical composition is provided in a container. The container can be one selected from the group of: a vial, an ampoule with a septum, a paper, a sachet, a syringe, an infusion bag, and a sealable bottle. In some embodiments, the syringe is a pre-filled syringe.

Embodiments are also directed to a method of conducting a photodynamic diagnosis (PDD) and/or photodynamic therapy or treatment (PDT) of a condition in a subject in need thereof, comprising administering a composition containing Form C to the subject. In some embodiments, the condition is one selected from the group of: a cancer, a pre-cancerous condition, a non-cancerous condition, a bacterial infection, a fungal infection, a viral infection, a parasitic infection, a prion infection, a bowel disorder and an infection associated with a cancer. In some embodiments, the condition is one selected from the group of: basal cell carcinoma, irritable bowel syndrome (IBS), colorectal cancer, stomach cancer, esophageal cancer, diverticular disease, infectious colitis, ulcerative colitis, Crohn's disease; ischemic colitis, radiation colitis, esophagitis, inflammatory bowel disease, small intestinal bacterial overgrowth, chronic pancreatitis, pancreatic insufficiency, hepatic encephalopathy, diarrhea, constipation, gastrointestinal motility disorders, gastroesophageal reflux disease (GERD), gastroparesis, chronic intestinal pseudo-obstruction (Ogilvie's syndrome), colonic pseudo-obstruction, functional heartburn, post-operative ileus, hypertrophic pyloric stenosis, dyspepsia (including functional dyspepsia or non-ulcer dyspepsia), gastrointestinal damage, anal fissure, achlorhydria, achalasia, hemorrhoids, intestinal polyps, gastrointestinal tract cancer, pancreatic cancer, prostatic cancer, gastrointestinal tract inflammation, a bacterial infection, bladder cancer, bone cancer, brain cancer, breast cancer, hematologic cancers, leukemia, liver cancer, lung cancer, non-small cell lung cancer, ovarian cancer, renal cell carcinoma, skin cancer, testicular cancer, throat cancer, thyroid cancer, uterine cancer, vaginal cancer, cervical cancer, pre-cancerous lesions of the cervix, HPV (human papilloma virus) infection, and inflammation of the uterine wall. In some embodiments, the bacterial infection is caused by at least one selected from the group of: *Bacillus cereus, Campylobacter jejuni, Escherichia coli, H. pylori, Listeria* spp., *Salmonella,* and *Shigella*.

In some embodiments, the composition is administered to the skin, bladder, uterus, vagina, ovary, testes, breast, lung, bone, mouth, pharynx, nose, ear, throat, central nervous system, liver, kidney, thyroid, blood, pancreas, stomach, colon and/or rectum of the subject.

Embodiments relate to a method of detecting and/or treating a condition in a subject, comprising: (i) administering a pharmaceutical composition comprising Form C to the subject, (ii) waiting for a period of time sufficient to allow the active ingredient to be converted to a photosensitizer and achieve an effective tissue concentration at a target site, e.g. a target site in the lower gastrointestinal area, (iii) photoactivating the photosensitizer and (iv) detecting a fluorescent signal from the photo sensitizer, wherein the presence of a fluorescent signal is indicative of the condition.

In some embodiments, the pharmaceutical composition is administered orally to the subject. In some embodiments, the pharmaceutical composition is administered by injection to the subject. In some embodiments, the composition is administered intravenously, subcutaneously, intramuscularly, or intraperitoneally to the subject. In some embodiments, the pharmaceutical composition is administered topically to the subject. In some embodiments, the composition is administered to the rectum of the subject. In some embodiments, the composition is administered vaginally to the subject. In some embodiments, the composition is administered by inhalation to the subject.

In some embodiments, the condition is one selected from the group of: a cancer, a pre-cancerous condition, a non-cancerous condition, a bacterial infection, a fungal infection, a viral infection, a parasitic infection, a prion infection, a bowel disorder or an infection associated with a cancer.

In some embodiments, the methods include administration of at least one dose of a purgative or a bowel preparation to the subject prior to administration of the pharmaceutical composition.

In a preferred embodiment, the invention provides a semi-solid pharmaceutical composition comprising a therapeutically effective amount of Form C, one or more triglycerides, and optionally one or more viscosity enhancers. It is preferred that the semi-solid pharmaceutical composition of is essentially water-free. The triglycerides used in the semi-solid pharmaceutical composition are preferably a mixture of medium chain triglycerides, with caprylic/capric triglycerides being particularly preferred. If the one or more triglycerides are liquid triglycerides, the presence of one or more viscosity enhancers in the composition is preferred. In a preferred embodiment, the semi-solid composition is an ointment and the amount of viscosity enhancer is adjusted such that an ointment is obtained. A preferred viscosity enhancer is stearic acid. In certain particularly preferred embodiments, the semi-solid pharmaceutical composition comprise about 0.2 to 5% (w/w) Form C, about 75 to 85% (w/w) caprylic/capric triglycerides, and about 15 to 20% (w/w) stearic acid. In certain embodiments of the invention, the semi-solid pharmaceutical composition is used in a method for the detection or treatment pre-cancerous lesions and cancer and/or HPV infection of the cervix, the anus, the penis, the vulva or the vagina, and preferably for the detection or treatment pre-cancerous lesions and cancer and/or HPV infection of the cervix In another embodiment, the invention provides a solid pharmaceutical composition comprising Form C where the solid pharmaceutical composition is in the form of a tablet, pellet, or capsule which has an enterosoluble and gastroresistant coating or in the form of a tablet or capsule which contains a plurality of pellets, pills, granules or mini-tablets coated with an enterosoluble and gastroresistant coating. Preferably, the enterosoluble and gastroresistant coating is pH-sensitive and it is particularly preferred that the pH-sensitive coating disintegrates or degrades at or about pH 6.5. In certain embodiments, the solid pharmaceutical composition further comprises one or more delayed release agents. The solid pharmaceutical compositions may preferably be used in methods of photodynamic treatment or diagnosis of cancer or a non-cancerous condition in the lower part of the gastrointestinal system. It is particularly preferred that the solid pharmaceutical composition is administered orally.

In another embodiment, the invention provides a powder, nanoparticle, or colloidal particle comprising a therapeutically or diagnostically effective amount of Form C for reconstitution in a solvent. The solution prepared from the Form C may be used in the treatment or detection of bladder cancer. The solution may be formed using and isotonic solution of a phosphate buffer, e.g. phosphate buffered saline (PBS). The solution may additionally comprise a local anesthetic and/or a chelating agent.

DETAILED DESCRIPTION

Figure 1:
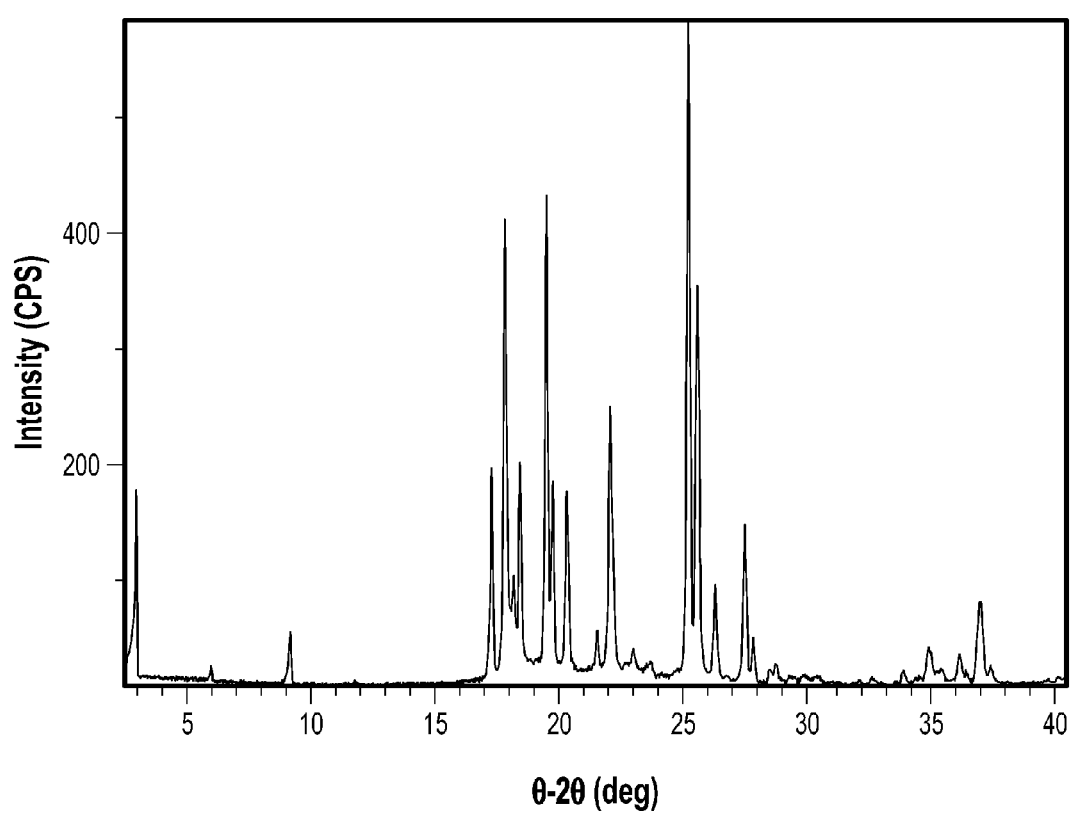
FIG. 1 is an exemplary X-ray powder diffraction (XRPD) pattern of the Form C as disclosed herein.

Form C, a new crystalline polymorph of hexyl 5-aminolevulinate hydrochloride (HAL) has been discovered which may have differing in vivo bioavailability properties. Thus, Form C disclosed herein can be useful in the preparation of pharmaceuticals with different characteristics for the photodynamic treatment and diagnosis of metabolically active cells, e.g. of a cancer, a pre-cancerous condition, a non-cancerous condition, a bacterial infection, a fungal infection, a viral infection, a parasitic infection, a prion infection, a bowel disorder or an infection associated with a cancer. This allows generation of HAL preparations that can have significantly different pharmacological properties from each other.

For example, different polymorphic forms of HAL can lead to preparations having different adsorption properties by subjects undergoing treatment and/or diagnosis.

Accordingly, embodiments are directed to a pharmaceutical product comprising a photo sensitizer which is Form C as disclosed herein, and at least one pharmaceutically acceptable carrier or excipient. In some embodiments, the pharmaceutical product is a solid pharmaceutical product. As used herein, the term "solid" refers to the physical state of the entity being described. Representative examples of solid pharmaceutical products include, but are not limited to, powders, a sterile packaged powder, granules, capsules, tablets, mini-tablets, pellets, pessaries and suppositories.

Embodiments are also directed to a pharmaceutical product comprising a photosensitizer which is Form C as disclosed herein, and at least one pharmaceutically acceptable carrier or excipient, in which the pharmaceutical product is a solution, an elixir, a suspension, an emulsion, a syrup, an aerosol, a sterile injectable solution, a cream, an ointment, or a lotion.

In some embodiments, the pharmaceutical product is a suppository, capsule, pellet, pessary, tablet, or mini-tablet. In some embodiments, the pharmaceutical product is provided in the form of a capsule containing a powder, pellet or granule composition. In some embodiments, the pharmaceutical product is provided in the form of a capsule containing a semi-solid or a liquid (including non-aqueous liquid) composition.

In embodiments where the product is provided in the form of pellets (e.g. tiny pills or mini-tablets), these can be administered as such. In some embodiments, the pellets can be incorporated into a tablet or capsule. Tablets or capsules comprising a plurality of pellets can be used in the methods as disclosed herein. Similarly, in embodiments where the product is provided in the form of a tablet, this can be administered as such. In some embodiments, the tablet can be incorporated into a capsule to provide a capsule-unit dose comprising a plurality of mini-tablets.

In some embodiments, the tablet or capsule can be coated. Capsule and tablet coatings suitable for these embodiments are described herein.

Form C, when used in the treatment or diagnoses of, for example, cancer of the uterus, cervix, vagina, rectum, colon, bladder, lower gastrointestinal tract, inflammatory bowel disease, ulcerative colitis, Crohn's disease, inflammatory bowel syndrome, dysplasia of the female reproductive system, anus, or penis, may take any conventional solid form, e.g. powder, granule, pellet, pessary, suppository, tablet or capsule, optionally with an enteric coating. In some embodiments Form C may be used in the preparation of a semi-solid dosage form, including a suspension; emulsion, cream; ointment; or lotion. In other embodiments, Form C may be used to prepare a solution for administration.

In some embodiments, the invention provides a solid pharmaceutical composition comprising Form C which is formulated for oral delivery, i.e. an oral solid pharmaceutical composition. The oral solid pharmaceutical composition is, for example, in the form of a tablet, pellet, or capsule. Preferred uses of such oral solid compositions are in the photodynamic treatment or diagnosis of cancerous or non-cancerous conditions in the lower gastrointestinal tract, e.g. in the treatment or diagnosis of colorectal cancer. The oral solid pharmaceutical composition comprising Form C is especially suitable for use in the photodynamic treatment or diagnosis of cancer or a non-cancerous condition in the lower part of the gastrointestinal system. In some embodiments, the oral solid pharmaceutical composition comprises an amount of Form C that is therapeutically effective for the treatment or diagnostically effective for the diagnosis of cancer in the lower gastrointestinal tract. In preferred embodiments, the cancer is colorectal cancer.

In certain embodiments of the invention, the oral solid pharmaceutical composition is for use in the photodynamic treatment or diagnosis of cancer, pre-cancerous and non-cancerous conditions in the lower part of the gastrointestinal system. In this embodiment, it is preferred that the composition reaches the lower part of the gastrointestinal system intact, i.e. without the active ingredient (Form C) being substantially released earlier. To achieve successful delivery to the lower gastrointestinal tract, the active ingredient is preferably protected from absorption and/or the environment of the upper gastrointestinal tract, e.g. stomach and upper small intestine and then is released into the lower gastrointestinal tract, i.e. the lower end of the small intestine and caecum. The oral solid pharmaceutical composition of Form C may be in the form of a capsule, tablet or pellet formulation having an enterosoluble and gastroresistant coating or in the form of a tablet or capsule which contains a plurality of pellets, pills, granules or mini-tablets coated with an enterosoluble and gastroresistant coating.

It is an advantage that the active ingredient is substantially homogenously (i.e. uniformly) distributed to the whole lower gastrointestinal tract. This is preferably accomplished by release of the active ingredient into the lower gastrointestinal tract, i.e. the lower end of the small intestine and caecum but also the distribution/spreading of the active ingredient from the place of release to the more distal parts of the colon and the rectum. This may be achieved by delayed release, i.e. the release of the active ingredient starts at the lower end of the small intestine and caecum and is delayed rather than abrupt, such that the pharmaceutical composition can travel through the colon with the active ingredient being released by and by. In another embodiment, this may be achieved by using two or more oral solid pharmaceutical compositions according to the invention with different release profiles or one oral solid pharmaceutical composition, e.g. a capsule, comprising e.g. mini-tablets, pellets or granules with different release profiles.

In some embodiments, the capsule or tablet is coated with at least one enteric coating. In some embodiments, the at least one enteric coating allows for the pH controlled release of the Form C in the range of a pH of about 5.5 to a pH of about 7.5. In some embodiments, the at least one enteric coating is selected from the group of: Eudragit® S 100, Eudragit® L100, TEC and talc.

In some embodiments, the oral solid pharmaceutical composition comprising Form C further comprises one or more delayed release agents comprising one or more amphiphilic delayed release agents comprising fatty acid esters of glycerol and one or more of polyethylene glycol (PEG) esters and polyglycolised glycerides, wherein the delayed release agents have a melting point of from about 33° C. to about 64° C. and an HLB value of from about 1 to about 14, and further wherein said pharmaceutical composition is provided in the form of a capsule coated with an enterosoluble and gastroresistant coating and wherein the coating is pH-sensitive. In some embodiments, the delayed release agent has a melting point of from about 35° C. to about 55° C. and an HLB value of from about 7 to about 14.

The solid oral pharmaceutical composition comprising Form C may be provided in the form of a tablet or capsule which contains a plurality of pellets, pills, granules or mini-tablets coated with an enterosoluble and gastroresistant coating. In some embodiments, the solid pharmaceutical composition comprising Form C further includes an anti-cancer agent.

In some embodiments, the oral solid pharmaceutical composition comprising Form C further comprises an oil, the oil comprising esters of saturated coconut and palm kernel oil-derived caprylic and capric fatty acids and glycerin or propylene glycol, and further wherein the pharmaceutical composition is provided in the form of a capsule coated with an enterosoluble and gastroresistant coating and wherein the coating is pH-sensitive. In some embodiments, the pH-sensitive coating disintegrates or degrades at about pH 6.5.

In some embodiments of the oral solid pharmaceutical composition comprising Form C, the plurality of pellets, granules, pills or mini-tablets provide different release profiles of the Form C after administration.

There are various known methods and systems for oral colonic delivery of pharmaceutical active ingredients which are based on an oral solid pharmaceutical product which comprises one or more pharmaceutical excipients that provide for controlled release of the active ingredient and/or by coating the oral pharmaceutical composition with a coating that provides such a time controlled release.

For purposes of oral administration, tablets containing various excipients agar, alginic acid, ascorbic acid, amino acids, calcium salts (e.g. calcium hydrogen phosphate), ammonium salts (e.g. ammonium acetate), carbomers, carbopols, cellulose compounds and derivatives (e.g. microcrystalline cellulose, methylcellulose, ethylcellulose, hydroxyethyl cellulose, hydroxypropylcellulose), citric acid, starch compounds and derivatives (e.g. corn starch, croscaramellose, crospovidone, cyclodextrins such as beta-cyclodextrin, lactose such as anhydrous lactose or lactose hydrate, maltodextrin, mannitol), menthol, synthetic polymers (e.g. methacrylic acid copolymers), polyethylene glycol derivatives (e.g. polysorbate), potassium salts (e.g. potassium hydrogen phosphate), sodium salts (e.g. sodium carbonate), povidone, sorbitan derivatives, talcum, wax, polyethylene glycol, poloxamer, medium-chain triglycerides, glycerides of $C_{8-18}$ fatty acids (e.g. hard fat) and mixtures thereof. MIGLYOL® oils, which are esters of saturated coconut and palm kernel oil-derived caprylic and capric fatty acids and glycerin or propylene glycol, are particularly preferred for use in the invention. These may, for example, be used when forming liquid-containing capsules containing Form C. Other forms and uses of oral administration of Form C is described in US Publication 2011/0220441A1, which is hereby incorporated by reference.

Further pharmaceutical excipients and carriers that may be used in the pharmaceutical compositions herein described are listed in various handbooks (e.g. Remington's, The Science and Practice of Pharmacy, (Gennaro, A. R., ed., 19th edition, 1995, Mack Pub. Co.) which is herein incorporated by reference, D. E. Bugay and W. P. Findlay (Eds) Pharmaceutical Excipients (Marcel Dekker, New York, 1999), E-M Hoepfner, A. Reng and P. C. Schmidt (Eds) Fiedler Encyclopedia of Excipients for Pharmaceuticals, Cosmetics and Related Areas (Edition Cantor, Munich, 2002) and H. P. Fielder (Ed), Lexikon der Hilfsstoffe für Pharmazie, Kosmetik and angrenzende Gebiete (Edition Cantor Aulendorf, 1989)).

Methods of oral delivery of Form C are described in US Publication Nos. 2012/0134921, and 2001/0020441 which are hereby incorporated by reference. Other relevant formulations with Form C and its modes and methods of use may be found in U.S. Pat. No. 6,034,267; U.S. Pat. No. 7,247,655; and U.S. Pat. No. 7,530,461 all of which are hereby incorporated by reference.

In other embodiments, the solid compositions of Form C according to the invention are provided in the form of a suppository. Suppository formulations may be formulated for use in the lower gastrointestinal system or in the female reproductive system for use in the photodynamic treatment or diagnosis of, for example, cancerous or non-cancerous conditions in the lower gastrointestinal tract or in the female reproductive system, e.g. pre-cancerous and cancerous lesions of the cervix, vagina or vulva and/or infections with human papilloma virus (HPV). The suppository may further comprise as one or more emulsifiers, lecithin, phosphatidylcholine, poloxamers, ethoxylated fatty alcohols or products obtained from the reaction of polyethylene glycol and natural or hydrogenated oils. Pharmaceutical compositions of Form C for use in the form of a suppository are described in US Publication Nos. 2012/0134921 and 2011/0020441, which are hereby incorporated by reference.

In other embodiments, the invention provides semi-solid compositions comprising Form C. For purposes of semi-solid embodiments, the composition according to the invention may be more or less fluid, e.g. an emulsion of the liquid, semi-liquid, soft or semi-solid consistency. It may have the appearance of a gel, cream, lotion, milk or liquid. The semi-solid compositions according to the inventions may be in the form of creams, ointments, pastes and gels for topical application to the skin and to mucous membranes.

The compositions according to the invention may comprise one or more emulsifiers, i.e. the composition according to the invention is an emulsion. The term "emulsifier" includes emulsifying agents, co-emulsifiers and agents with surfactant properties. The term "one or more" means that the composition according to the invention comprises one emulsifier or several different emulsifiers.

The one or more emulsifiers used in the composition of the invention may be any of the usual type of emulsifiers used for the preparation of compositions for use on the mammal skin, preferably for use on the human skin. In a preferred embodiment, the one or more emulsifiers used in the composition of the invention may be any of the usual type of emulsifiers used for the preparation of oil/water emulsions for use on the mammal, preferably human, skin. Such emulsifiers are e.g. non-ionic-, cationic-, anionic and betaine compounds with the non-ionic emulsifiers being high HLB emulsifiers, preferably emulsifiers with an HLB value of 8 to 18. The use of non-ionic or cationic emulsifiers is preferred, more preferred is the combined use of non-ionic and cationic emulsifiers, preferably the combined use of non-ionic emulsifiers with an HLB value of 8 to 18 and cationic emulsifiers.

The emulsifiers used in the composition according to the invention can be synthetic, semi-synthetic or natural compounds. Some specific examples of such compounds are: almondamidopropyl betaine, aminoethyl sulfate, 3-aminopropane sulfonic acid, alkyl sulfate salts, e.g. ammonium salts and other salts, ethoxylated alcohols (pareths), cholesterol esters, calcium lignosulfonate and other calcium sulfonic acid salts, calcium myristate and other calcium fatty acid salts, capric acid, capronic acid, capryleth carboxylic acids, polyoxyethylene ethers (ceteareths), e.g. ceteareth-20, PEG alkyl ethers (ceteths), ethoxylated unsaturated alcohols (cetoleths), fatty alcohols, e.g. cetyl alcohol, stearyl alcohol or mixtures thereof (cetearyl alcohol), ethoxylated docosanol (beheneths) and behentrimonium salts like behentrimonium methosulfate, ethoxylated cholesterol derivatives (choleths), cocamine and cocamides, emulsifying wax, diethanolamine alkyl sulfates, DEA-oleth-3 phosphate and similar phosphates, deceths and deceths phosphates, dextrin laurate and other dextrin fatty acid esters, disodium oleyl sulfosuccinate and other sulfosuccinate compounds, dodoxynols, glucereth stearate, glycereth phosphate, quaternary ammonium compounds, glyceride citrates and phosphates, hydroxycetyl phosphate, isosteareths, ethoxylated lanolin alcohols (laneths), lanolin and lanolin derivatives, laurylamides, ethoxylated dodecanol (laureths) and lauryltrimonium salts, magnesium laureth sulfates, meroxapols, methyl glucose laurate, methyl laurate, nonoxynols, octoxynols, octyldodeceths, oleths, palmamides, fatty esters of polyethylene glycol (PEG) such as PEG-100 stearate, PEG 50-stearate and PEG 40-stearate, PEG amines, ethoxylated castor oil and other ethoxylated oils and hydrophobic compounds, polyoxamers, poloxamines, polyglyceryl-2-distrearate and other esters, steareths and sorbeths, polysorbates (Tween) and esters of sorbitan (Span).

In some embodiments, the invention provides a semi-solid pharmaceutical composition comprising Form C and a) one or more triglycerides, and b) optionally, one or more viscosity enhancers.

In some embodiments, the one or more triglycerides are triglycerides of glycerol and 3 identical or different $C_2$-$C_{22}$ fatty acids, more preferably 3 identical or different $C_4$-$C_{18}$ fatty acids, even more preferably 3 identical or different $C_6$-$C_{18}$ fatty acids and most preferably 3 identical or different $C_6$-$C_{12}$ fatty acids. In some embodiments, the one or more triglycerides are liquid triglycerides and one or more viscosity enhancers are present to obtain such semi-solid pharmaceutical compositions. In some embodiments, the one or more viscosity enhancers are selected from cellulose and derivatives thereof, synthetic polymers, polyethylene glycols, vegetable gums, starch and starch derivatives, carrageenan, agar, gelatin, wax and waxy solids, preferably selected from a wax or a waxy solid, most preferably selected from a solid fatty alcohol or fatty acid.

In some embodiments, the semi-solid pharmaceutical composition comprising Form C further comprises:

c) optionally one or more emulsifiers, d) optionally one or more mucoadhesives, e) optionally one or more surface penetration agents, and f) optionally one or more chelating agents.

In some preferred embodiments, the semi-solid pharmaceutical composition is water-free.

In some preferred embodiments, the one or more triglycerides is a liquid triglyceride, preferably selected from triglycerides of glycerol and 3 identical or different $C_2$-$C_{22}$ fatty acids, more preferably 3 identical or different $C_4$-$C_{18}$ fatty acids, even more preferably 3 identical or different $C_6$-$C_{18}$ fatty acids and most preferably 3 identical or different $C_6$-$C_{12}$ fatty acids and the one or more viscosity enhancers are present.

Preferred triglycerides include tricaprylin, tricaproin, triheptanoin, caprylic/capric triglyceride and caprylic/capric/linoleic triglyceride and caprylic/capric/succinic triglyceride. Some of these triglycerides are marketed under the name "Miglyol®", e.g. with Miglyol 812 being caprylic/capric triglyceride, Miglyol 818 being caprylic/capric/linoleic triglyceride and Miglyol 808 being tricaprylin. A manufacturer or such triglycerides is for instance Sasol, Witten, Germany.

Preferred semi-solid compositions are the ointments shown in the table below.

| Ingredient | Purpose | Semi-solid pharmaceutical composition 1 | | Semi-solid pharmaceutical composition 2 | | Semi-solid pharmaceutical composition 2 | |
|---|---|---|---|---|---|---|---|
| | | % (w/w) | Amount (g) | % (w/w) | Amount (g) | % (w/w) | Amount (g) |
| Form C | Active ingredient | 5 | 175 | 1 | 40 | 0.2 | 8 |
| Miglyol 812 | Trigryceride | 77 | 2695 | 80.2 | 3208 | 80.8 | 3232 |
| Stearic acid | Viscosity enhancer | 18 | 630 | 18.8 | 752 | 19 | 760 |
| Sum | | 100 | 3500 | 100 | 4000 | 100 | 4000 |

The term "viscosity enhancer" denotes a compound that thickens or stiffens a mixture of Form C and other ingredients in the semi-solid pharmaceutical composition. Examples of viscosity enhancers are cellulose and derivatives thereof like carboxymethylcellulose sodium, hydroxyethylcellulose (HEC), hydroxypropyl methylcellulose (HPMC), methylcellulose (MC), synthetic polymers like polyacrylic acid (carbomer), polyethylene glycols, vegetable gums like guar gum, gum arabic or tragacanth, starch and starch derivatives, carrageenan, agar, gelatin, wax and waxy solids. In some embodiments, the one or more viscosity enhancers are selected from a wax or a waxy solid, most preferably selected from a solid fatty alcohol or fatty acid. The viscosity enhancer may be stearyl alcohol, stearic acid, or cetostearyl alcohol, which is a mixture of fatty alcohols, consisting predominantly of cetyl and stearyl alcohols.

In a preferred embodiment, the semi-solid pharmaceutical compositions are water-free compositions which do not contain any glycols or glycerols. In a further preferred embodiment, the semi-solid pharmaceutical compositions consist of Form C, one or more triglycerides and optionally one or more viscosity enhancers. In a preferred embodiment, such semi-solid pharmaceutical compositions comprise Form C in an amount of 0.1 to 10% by weight, more preferably 0.1 to 6% by weight and most preferably 0.2 to 5% by weight.

In a preferred embodiment, the semi-solid pharmaceutical compositions comprising Form C are for use in photodynamic treatment of pre-cancerous, cancerousl and non-cancerous conditions in the female reproductive system, the anus and the penis, preferably for use in photodynamic treatment of dysplasia and HPV infections in the female reproductive system, the anus and the penis, more preferably endometrial, cervical, vaginal, vulvar, anal and penile dysplasia and HPV infections of the uterus, cervix, vagina, vulva, anus and penis. In a more preferred embodiment, the semi-solid pharmaceutical compositions comprising Form C are for use in photodynamic treatment of endometrial, cervical, vaginal and vulvar dysplasia and HPV infections in the uterus, cervix, vagina and vulva. In a most preferred embodiment, the semi-solid pharmaceutical compositions comprising Form C are for use in photodynamic treatment of cervical and vaginal dysplasia and HPV infections in the cervix and vagina. In this context, the semi-solid pharmaceutical compositions comprising Form C may be used with the irradiation device that is described herein. Form C may be formulated in semi-solid pharmaceutical compositions according to the disclosures of US Publication 2012/0136055, the disclosures of which are incorporated herein by reference for this purpose.

In another embodiment, the invention provides semi-solid compositions comprising Form C for application to the skin. The semi-solid compositions may further comprise one or more dermal adjuvants, i.e. adjuvants which are commonly used in compositions for use on the skin, e.g. preserving agents, antimicrobial agents, fragrances, coloring agents, colorants, dyestuffs, fillers, pigments, antioxidants, solvents, viscosity modifiers (e.g. thickening agents) and/or pH-adjusters/modifiers. Dermal adjuvants are known in the art and dermal adjuvants conventionally used in cosmetic and pharmaceutical dermal products may be used in the compositions of the invention. Such dermal adjuvants may be used in the composition of the invention in an amount which is conventionally used in cosmetic and pharmaceutical dermal products. Said amount can vary, for example, from approximately 0.01 to 10% by weight, preferably from 0.1 to 5% by weight. Cosmetic compositions of Form C are described in US Publication No. 2011/0212146, which is hereby incorporated by reference.

Such semi-solid compositions according to the invention may be used together with other cosmetic or pharmaceutical products containing known anti-aging or anti-wrinkle agents. Such other cosmetic or pharmaceutical products may be co-administered or preferably administered after the treatment with the compositions herein described. The compositions according to the invention may also be used in combination with other cosmetic and/or therapeutic methods which are known and described in the literature for use in the treatment of (photo)aged skin, such as chemical peelings, microdermabrasions or cosmetic injectables like Botox™ or fillers.

Another embodiment of the invention is directed to the detection and/or treatment of urological lesions, e.g. lesions in the bladder or the urethra, and particularly bladder cancers, using Form C. In one embodiment, the invention comprises application of a solution of hexyl-5-aminolevulinate HCl formed by dissolving a solid pharmaceutical product comprising Form C to detect and/or treat urological lesions such as bladder cancer, for example carcinoma in situ, papillary lesions and invasive carcinoma, In a preferred embodiment, the present invention provides the use of a solution of hexyl-5-aminolevulinate HCl formed by dissolving a solid pharmaceutical product comprising Form C for the detection of cancers of the bladder, particularly in patients that are suspected or are known to have lesions, for example on the basis of prior cystoscopy.

Form C, when used to detect and/or treat urological lesions, may take on the form of a powder, nanoparticles, colloidal particles or other solid form which may be reconstituted in a solvent. Preferably, the solution formed from Form C in an appropriate solvent is applied to the bladder or the urethra using a catheter.

For the treatment and detection of urological lesions, e.g. bladder cancer, the dosage form is preferably an isotonic solution prepared from Form C, for example by dissolution with a suitable buffer such as phosphate buffered saline (PBS), optionally containing carriers or excipients such as local anesthetic (e.g. lidocaine) and chelating agents (e.g. EDTA or desferroxamine). An example of such a solution is 4.3 mM $KH_2PO_4$, 4.3 mM $Na_2HPO_4$, 120.1 mM NaCl, pH 5.8-6.3, containing 4-16 mM hexyl-5-aminolevulinate HCl for diagnosis, preferably 8 mM hexyl-5-aminolevulinate HCl, wherein the solution is prepared from Form C.

For the treatment or detection of bladder cancer, the invention may be administered to the bladder for a period of time which can range, for example, from 0.5 to 4 hours. The inside of the bladder is subsequently exposed to photoactivating light, for example 0 to 2 hours following administration of the above-described solution.

Formulations and methods relating to the diagnoses and treatment of urological lesions, e.g. bladder cancer, may additionally be found in U.S. Pat. Nos. 6,034,267, 7,247,655, 7,348,361 and 7,530,461, each of which is incorporated herein by reference.

In another embodiment, the invention provides a dry pharmaceutical composition, wherein said dry pharmaceutical composition comprises:
a) Form C;
b) optionally one or more polymers which have good film-forming properties and/or good gel-forming properties; and
c) optionally other pharmaceutically acceptable excipients.

In a preferred embodiment, the invention provides an irradiation device for use in photodynamic therapy which comprises, in an area for carrying a pharmaceutical composition, a dry pharmaceutical composition, wherein said dry pharmaceutical composition comprises:
a) Form C;
b) optionally one or more polymers which have good film-forming properties and/or good gel-forming properties; and
c) optionally other pharmaceutically acceptable excipients.

In a another preferred embodiment, the invention provides an irradiation device for use in photodynamic therapy or photodynamic diagnosis of cancerous, pre-cancerous and non-cancerous conditions of the cervix, the vagina, the rectum, the anus, the nose or the ear which comprises, in an area for carrying a pharmaceutical composition, a dry pharmaceutical composition, wherein said dry pharmaceutical composition comprises:
a) Form C;
b) optionally one or more polymers which have good film-forming properties and/or good gel-forming properties; and
c) optionally other pharmaceutically acceptable excipients.

In yet another preferred embodiment, the invention provides an irradiation device for use in photodynamic therapy of cancerous, pre-cancerous and non-cancerous conditions of the cervix, the vagina, the rectum, the anus, the nose or the ear which comprises, in an area for carrying a pharmaceutical composition, a dry pharmaceutical composition, wherein said dry pharmaceutical composition comprises:
a) Form C;
b) optionally one or more polymers which have good film-forming properties and/or good gel-forming properties; and
c) optionally other pharmaceutically acceptable excipients.

Whilst it is preferred that such pharmaceutical compositions should be substantially free from any solvent (e.g. water), these may nonetheless contain residual solvent. The term "dry" should thus be construed accordingly. Preferred compositions are those which are substantially solvent free, for example those prepared by any of the processes herein described. Such processes need not involve the use of any subsequent means to further reduce or eliminate any residual solvent. As noted above, the use of dry compositions ensures that the above-mentioned devices (which includes the composition) have a long shelf life.

Embodiments of such dry pharmaceutical compositions are disclosed in WO 2012/004399 and embodiments of the devices mentioned above are disclosed in WO 2010/078929, each of which is incorporated herein by reference in its entirety.

Active Agents

In the disclosure provided infra, the term "active ingredient" (also referred to as "the photosensitizing agent" or "the photosensitizer") refers to Form C as disclosed herein. Form C as described herein comprise X-ray powder diffraction (XRPD) pattern peak positions as denoted in the Tables, Examples and Figures disclosed herein.

As used herein, the term "about" when used in reference to XRPD pattern peak positions refers to the inherent variability of the peaks depending on, for example, the calibration of the equipment used, the process used to produce Form C, the age of the crystallized material and the like, and/or the instrumentation used. In this case the measurement variability of the instrument was about ±0.2 degrees 2θ, which is consistent with the USP definition for peak position error. A person skilled in the art, having the benefit of this disclosure, would understand the use of "about" in this context. The term "about" in reference to other defined parameters, e.g., water content, $C_{max}$, $t_{max}$, AUC, intrinsic dissolution rates, temperature, and time, indicates the inherent variability in, for example, measuring the parameter or achieving the parameter. A person skilled in the art, having the benefit of this disclosure, would understand the variability of a parameter as connoted by the use of the word "about."

As used herein, "similar" in reference to a form exhibiting characteristics similar to, for example, an XRPD, an infrared (IR), a Raman spectrum, a differential scanning calorimetry (DSC), TGA, NMR, solid state NMR (SSNMR), etc, indicates that the polymorph is identifiable by that method and could range from similar to substantially similar, so long as the material is identified by the method with variations expected by one of skill in the art according to the experimental variations, including, for example, instruments used, time of day, humidity, season, pressure, room temperature, etc.

Polymorphism, as used herein, refers to the occurrence of different crystalline forms of a single compound in distinct hydrate status, e.g., a property of some compounds and complexes. Thus, polymorphs are distinct solids sharing the same molecular formula, yet each polymorph can have distinct physical properties. Therefore, a single compound can give rise to a variety of polymorphic forms where each form has different and distinct physical properties, such as solubility profiles, melting point temperatures, hygroscopicity, particle shape, density, flowability, compactibility and/or X-ray diffraction peaks. The solubility of each polymorph can vary, thus, identifying the existence of pharmaceutical polymorphs is desirable for providing pharmaceuticals with consistent and reproducible solubility profiles. Polymorphic forms of a compound can be distinguished in a laboratory by X-ray diffractometry and by other methods such as infrared spectroscopy. For a general review of polymorphs and the pharmaceutical applications of polymorphs see G. M. Wall, *Pharm Manuf.* 3, 33 (1986); J. K. Haleblian and W. McCrone, *J Pharm. Sci.*, 58, 911 (1969); and J. K. Haleblian, *J. Pharm. Sci.*, 64, 1269 (1975), each of which is incorporated herein by reference in its entirety.

The language "a prophylactically effective amount" of a compound refers to an amount of Form C described herein, or otherwise as described herein which is effective, upon single or multiple dose administration to the subject, in preventing or treating a cancer, a pre-cancerous condition, a non-cancerous condition, a bacterial infection, a bowel disorder or an infection associated with a cancer.

As used herein the term "treatment" encompasses curative as well as prophylactic treatment. The language "therapeutically effective amount" of a compound refers to an amount of Form C which is effective, upon single or multiple dose administration to the subject to provide a therapeutic benefit to the subject. In some embodiments, the therapeutic benefit is inhibiting a virus, or in prolonging the survivability of a subject with such a viral infection. In some embodiments, the therapeutic benefit is inhibiting a bacterial infection or prolonging the survival of a subject with such a bacterial infection beyond that expected in the absence of such treatment.

For XRPD analysis, accuracy and precision associated with measurements on independently prepared samples on different instruments can lead to variability which is greater than ±0.2° 2θ.

Form C described herein can also be characterized by unit cell volume. One of skill in the art would be able to determine major peaks and uniquely identifying peaks of the polymorphs of HAL, e.g. Form C, using the information set forth herein as well as the peak lists and XPRD patterns and data.

Figure 2:
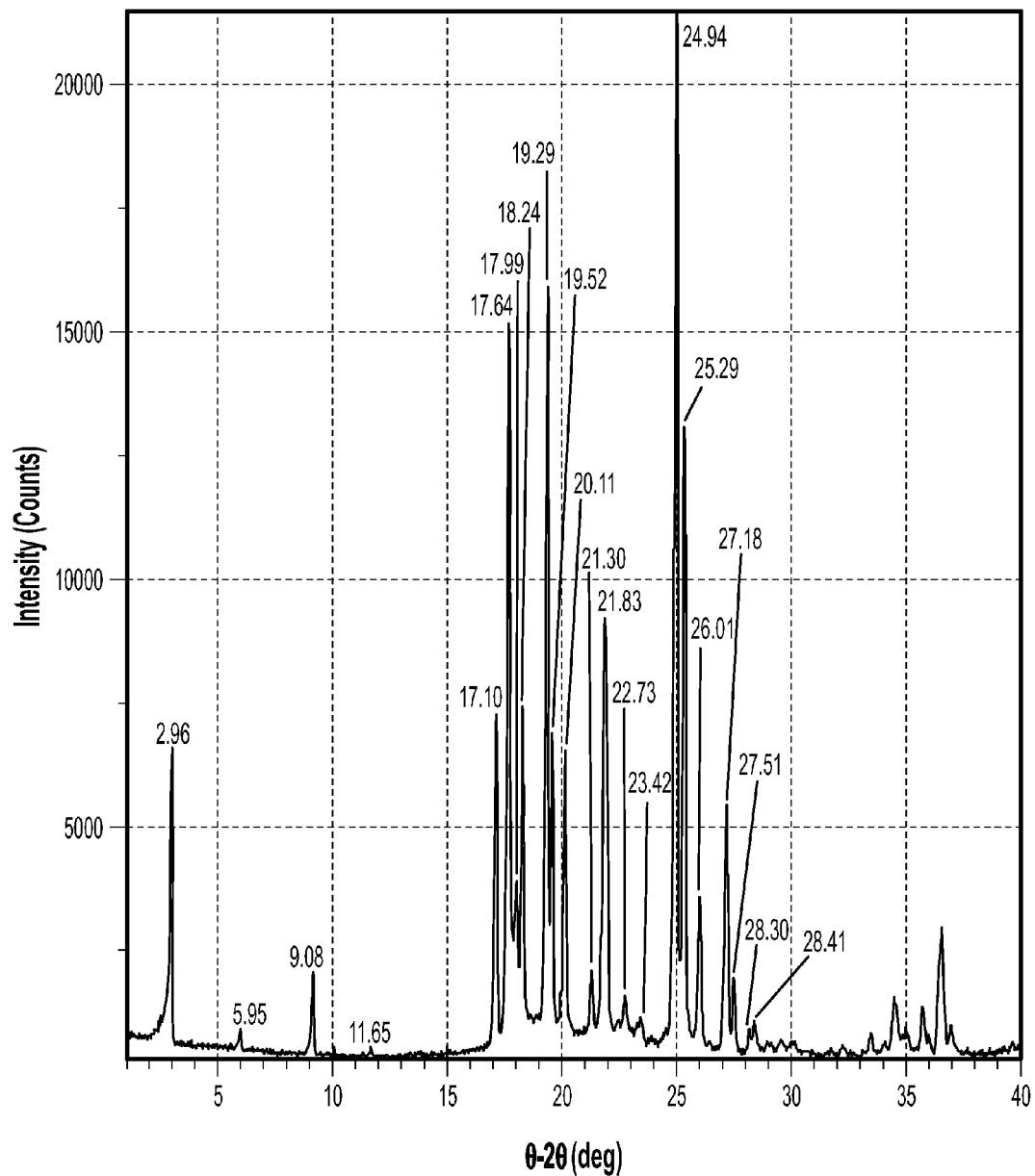
FIG. 2 is an exemplary X-ray powder diffraction (XRPD) pattern of the Form C as disclosed herein.

In some embodiments, Form C comprises an XRPD substantially similar to FIG. 1 or FIG. 2.

Figure 3:
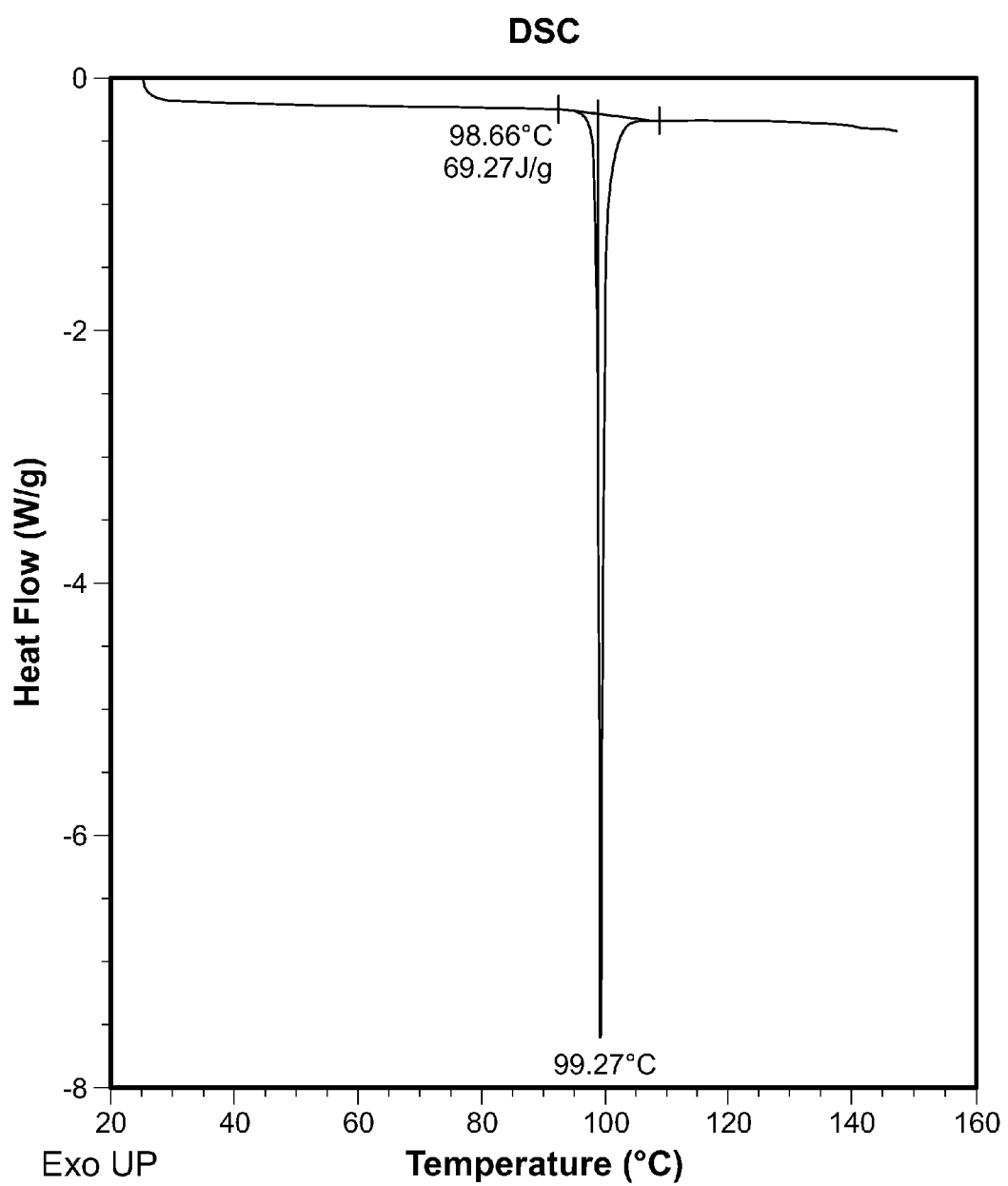
FIG. 3 is a differential scanning calorimetry (DSC) thermogram of the Form C as disclosed herein.
Figure 4:
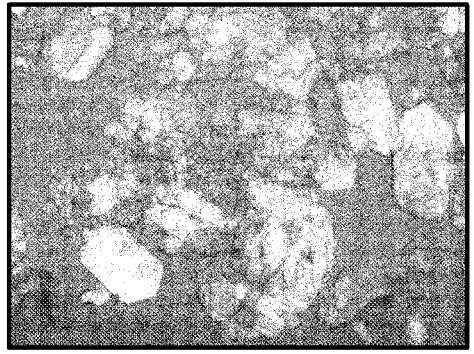
FIG. 4 are hot-stage microscopy photomicrographs of the Form C as disclosed herein.
Figure 4:
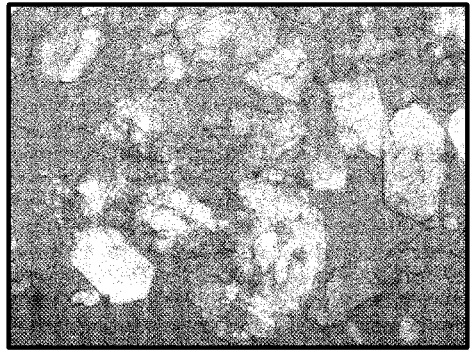
Figure 4:
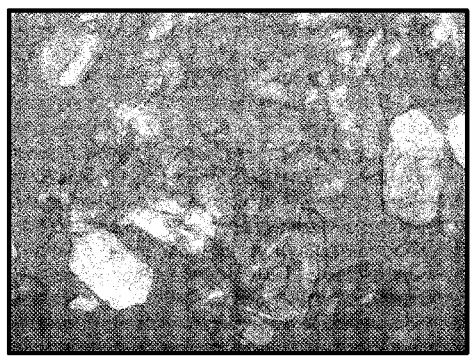
Figure 4:
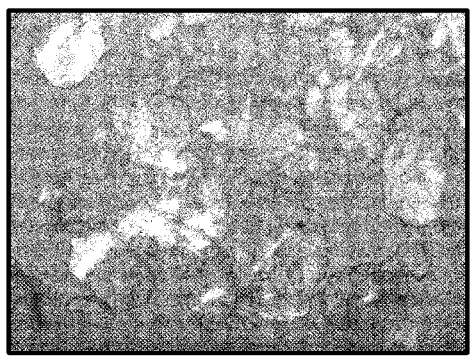
Figure 4:
Figure 10:
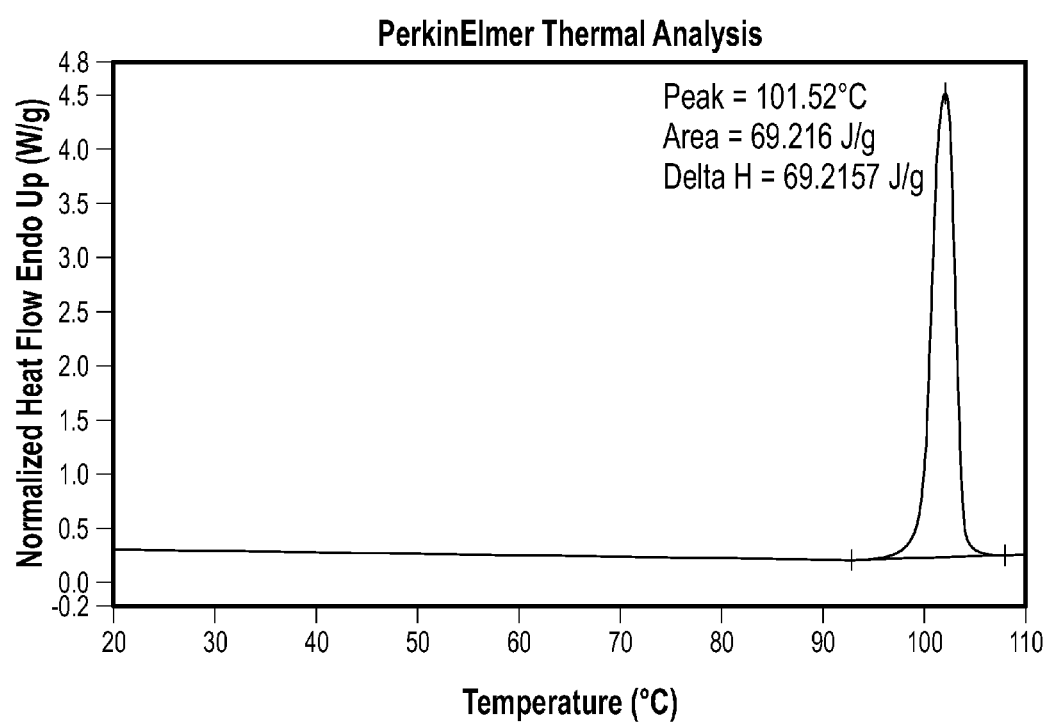
FIG. 10 is a differential scanning calorimetry (DSC) thermogram of Form C as disclosed therein.

In some embodiments, Form C comprises a DSC or TGA thermogram substantially similar to FIG. 3 or to FIG. 10.

Figure 5:
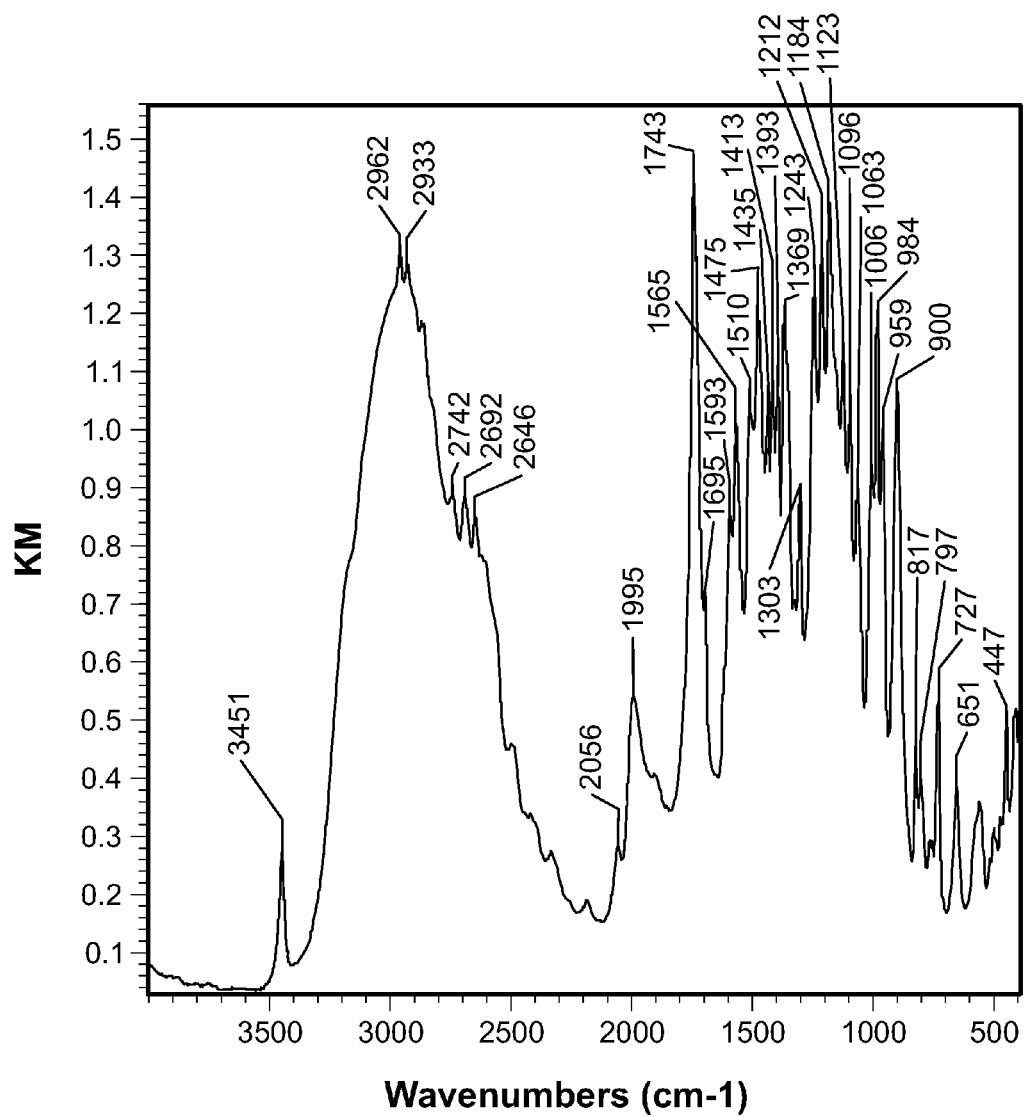
FIG. 5 is an exemplary infrared spectrum of the Form C as disclosed herein.

In some embodiments, Form C comprises an infrared spectrum substantially similar to that of FIG. 5.

Figure 6:
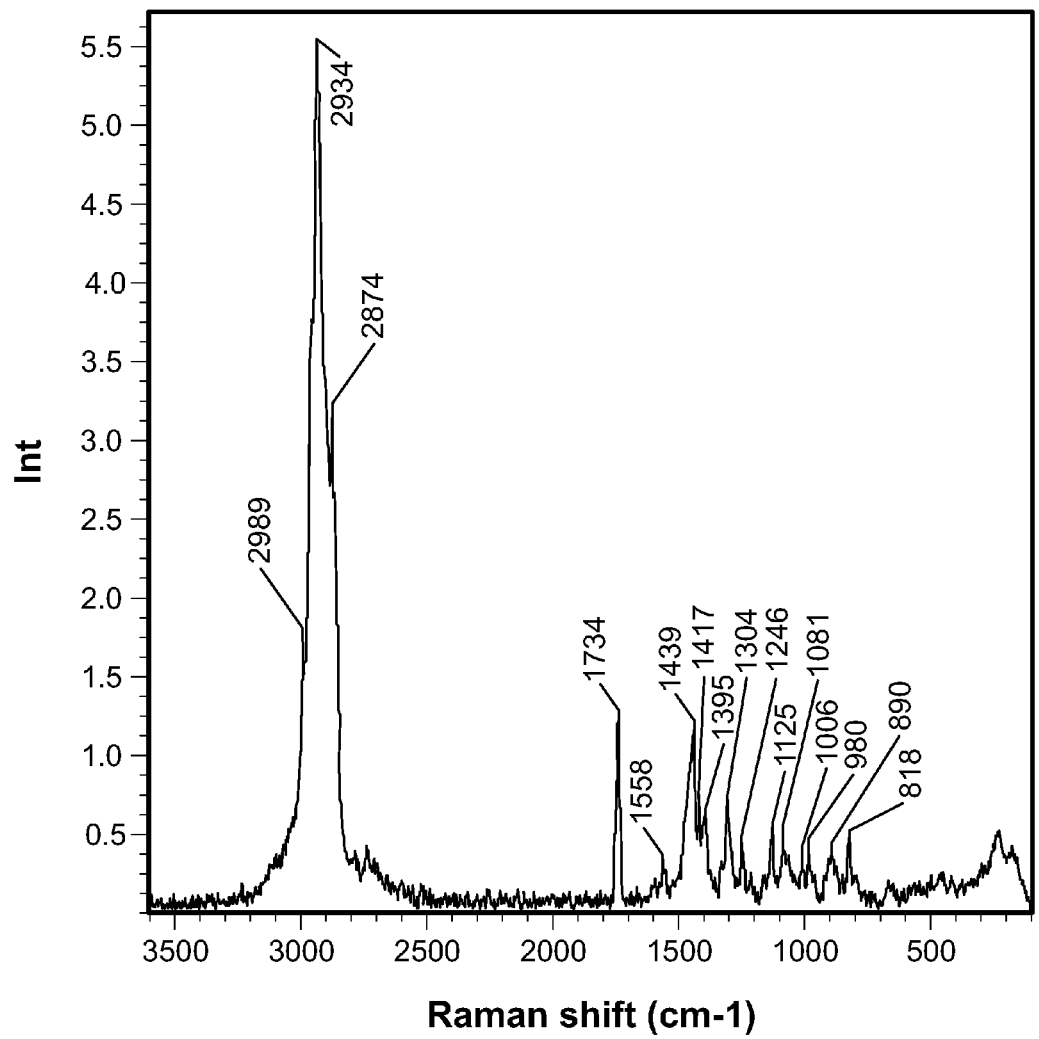
FIG. 6 is an exemplary Raman spectrum of the Form C as disclosed herein.

In some embodiments, Form C comprises a Raman spectrum substantially similar to that of FIG. 6.

Figure 7:
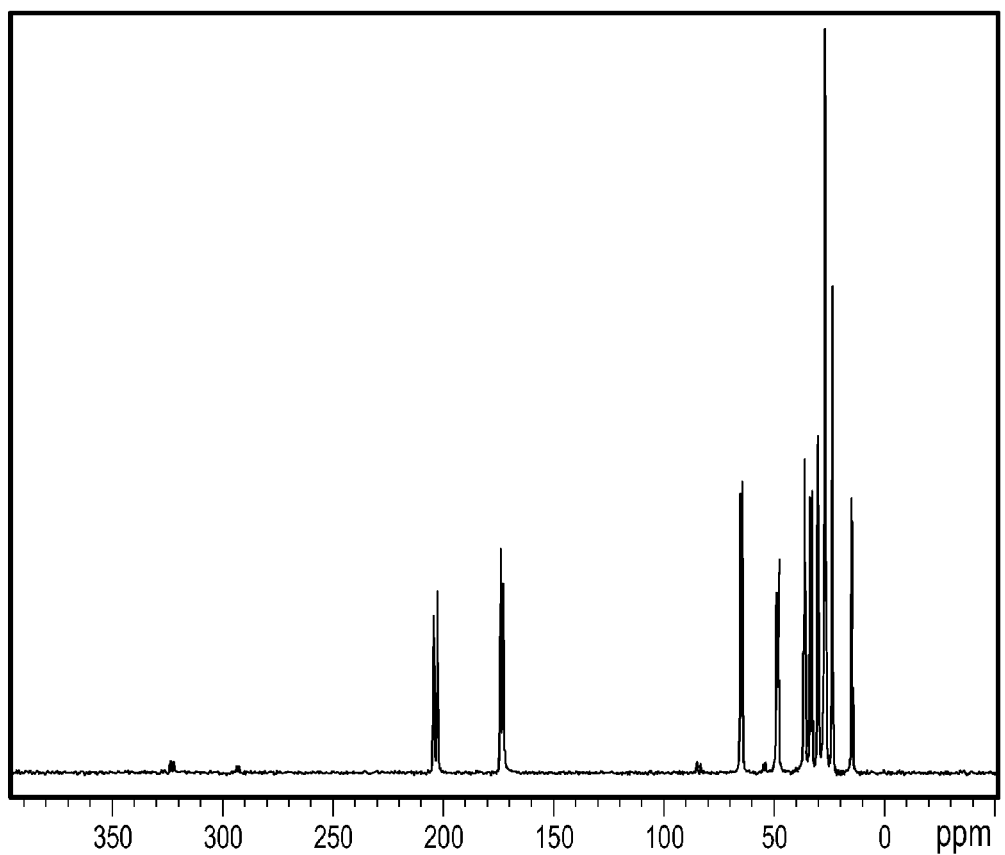
FIG. 7 is an exemplary solid state carbon NMR spectrum of the Form C as disclosed herein.
Figure 8:
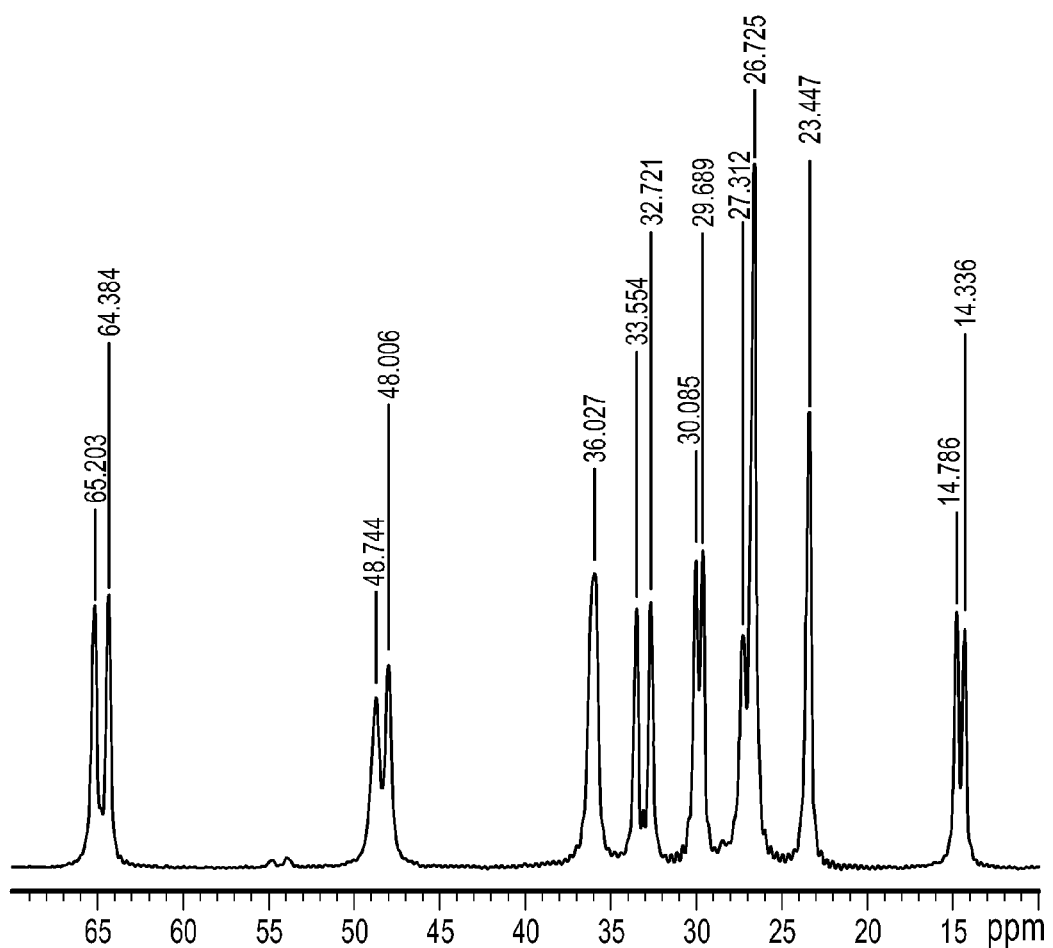
FIG. 8 is an exemplary solid state carbon NMR spectrum (from 70 ppm to 10 ppm) of the Form C as disclosed herein.
Figure 9:
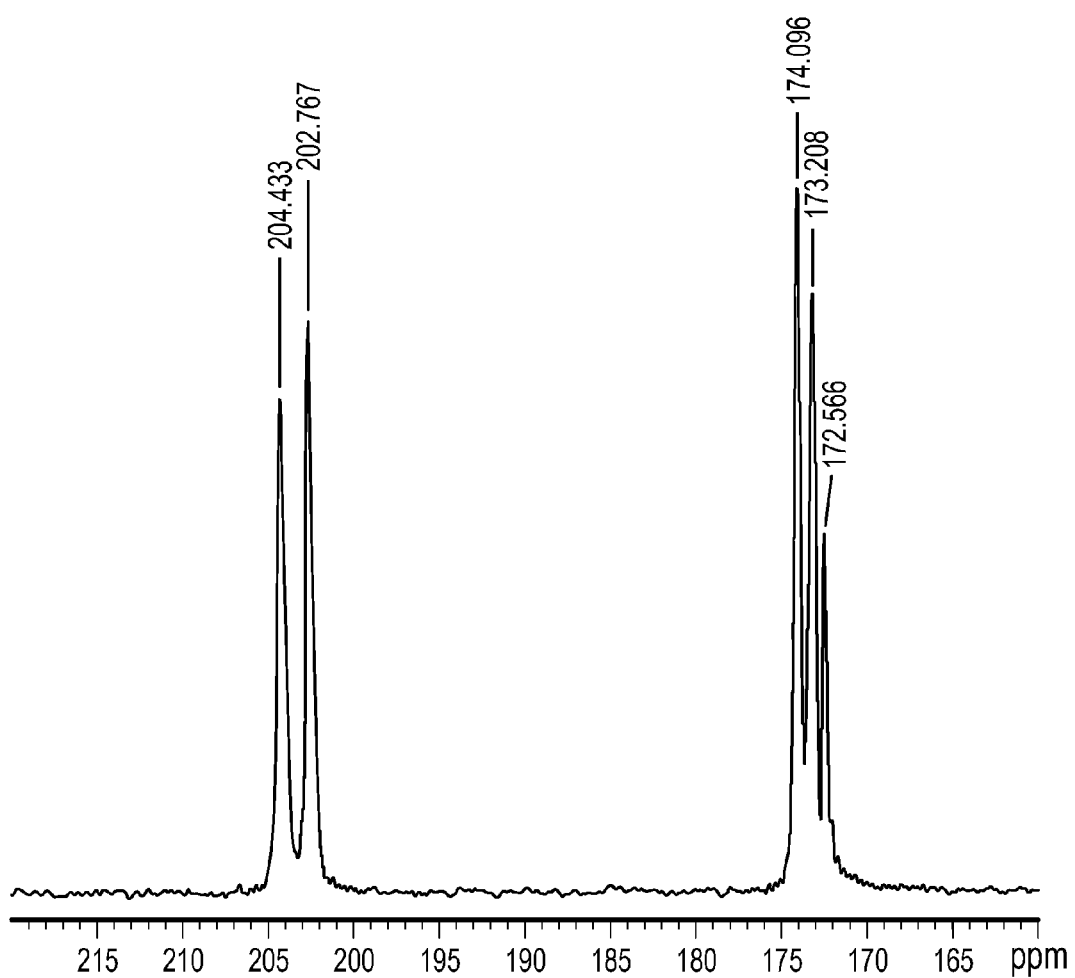
FIG. 9 is an exemplary solid state carbon NMR spectrum (from 215 ppm to 160 ppm) of the Form C as disclosed herein.

In some embodiments, Form C comprises a solid state carbon NMR spectrum substantially similar to that of any one of FIGS. 7-9.

In some embodiments, Form C comprises at least two XRPD peaks listed in any of Tables 1 and 2.

In some embodiments, Form C comprises at least two infrared spectrum peaks listed in any of Tables 3 and 4.

In some embodiments, Form C comprises at least two Raman spectrum peaks listed in any of Tables 5 and 6.

In some embodiments, Form C comprises at least two chemical shifts for solid state NMR listed in Table 7.

In some embodiments, Form C exhibits an X-ray powder diffraction pattern comprising peaks expressed in degrees 2θ comprising one or more peaks listed in FIG. 1 or FIG. 2.

In some embodiments, Form C exhibits an X-ray powder diffraction pattern comprising peaks expressed in degrees 2θ at two or more of about 2.96, about 5.95, about 9.08, about 11.65, about 17.10, about 17.64, about 17.99, about 18.24, about 19.29, about 19.52, about 20.11, about 21.30, about 21.83, about 22.73, about 23.42, about 24.94, about 25.29, about 26.01, about 27.18, about 27.51, about 28.20, and about 28.41.

In some embodiments, Form C exhibits an X-ray powder diffraction pattern comprising peaks expressed in degrees 2θ at two more of about 17.64, about 19.29, and about 24.94.

In some embodiments, Form C exhibits an X-ray powder diffraction pattern comprising peaks expressed in degrees 2θ at two more of about 19.29, about 24.94, and about 25.29.

In some embodiments, Form C exhibits an X-ray powder diffraction pattern comprising peaks expressed in degrees 2θ at two more of about 17.64, about 19.29, and about 25.29.

In some embodiments, Form C exhibits an X-ray powder diffraction pattern comprising peaks expressed in degrees 2θ at two more of about 17.64, about 24.94, and about 25.29.

In some embodiments, Form C exhibits an X-ray powder diffraction pattern comprising peaks expressed in degrees 2θ at two more of about 19.29, about 21.83, and about 24.94.

In some embodiments, Form C exhibits an X-ray powder diffraction pattern comprising peaks expressed in degrees 2θ at two more of about 17.64, about 21.83, and about 24.94.

In some embodiments, Form C exhibits an X-ray powder diffraction pattern comprising peaks expressed in degrees 2θ at about 17.64, about 19.29, about 21.83, about 24.94, and about 25.29.

In some embodiments, Form C exhibits an X-ray powder diffraction pattern comprising peaks expressed in degrees 2θ at about 2.96, about 17.10, about 17.64, about 18.24, about 19.29, about 19.52, about 20.11, about 21.83, about 24.94, and about 25.29.

In some embodiments, Form C exhibits an X-ray powder diffraction pattern comprising peaks expressed in degrees 2θ at about 2.96, about 17.10, about 17.64, about 18.24, about 19.29, about 19.52, about 20.11, about 21.83, about 24.94, about 25.29, about 26.01, and about 27.18.

In some embodiments, Form C exhibits an X-ray powder diffraction pattern comprising peaks expressed in degrees 2θ at about 2.96, about 9.08, about 17.10, about 17.64, about 17.99, about 18.24, about 19.29, about 19.52, about 20.11, about 21.83, about 24.94, about 25.29, about 26.01, and about 27.18.

In some embodiments, Form C contains less than 5% by weight total impurities.

In some embodiments, Form C is at least 50% pure, or at least 75% pure, or at least 80% pure, or at least 90% pure, or at least 95% pure, or at least 98% pure.

The new Form C can be prepared as follows: A solution of hexyl 5-aminolevulinate hydrochloride in acetonitrile, 158 mg in 1 ml, is heated to about 55° C. The solution is filtered through a 0.2 μm nylon filter into about 5 ml of refluxing hexanes (temperature=67° C.). The refluxing solution is stirred at 200 rotations per minute (rpm). The volume is reduced, through evaporation, until solids are observed. An additional 5 ml of refluxing hexanes is added, and the slurry is refluxed for approximately 5 minutes. The new Form C is harvested by vacuum filtration and dried under nitrogen at room temperature.

Accordingly, in some embodiments, methods for producing Form C comprise: obtaining a solution of hexyl 5-aminolevulinate hydrochloride in acetonitrile; heating the solution to at least about 55° C. with or without stirring; filtering the solution, wherein the filtrate is added to a small volume of refluxing heptanes held at a temperature of at least about 67° C. to form a second solution; reducing the volume of the second solution until solids are observed; optionally adding a second small volume of refluxing heptanes and evaporating the volume of the resulting slurry until solids are observed; and harvesting the solids, thereby producing Form C. In some embodiments, the small volume of refluxing heptanes comprises between about 5 and 15 mL of refluxing heptanes.

Form C can also be prepared as follows: Form C is prepared by exposing a solid sample of hexyl 5-aminolevulinate hydrochloride to a temperature of about 80° C. for approximately 3 to 6 hours or more.

Accordingly, in some embodiments, methods for producing Form C comprise: exposing a solid sample of hexyl 5-aminolevulinate hydrochloride to a temperature of at least about 80° C., thereby producing Form C. In some embodiments, the solid sample is exposed to a temperature of about 80° C. In some embodiments, the solid sample is exposed to a temperature of at least about 80° C. for about 3, 4, 5, or 6 hours or more. In some embodiments, the solid sample of hexyl 5-aminolevulinate hydrochloride is exposed to a temperature of at least about 80° C. for at least about 3 hours.

Pharmaceutical Products

The compounds as disclosed herein can be used for the manufacture of a pharmaceutical product in any manner. The desired concentration of photosensitizer in the pharmaceutical products of the invention will vary depending on several factors including the nature of the compound, the nature and form of the product in which the product is presented, the intended mode of administration, the nature of the cancer, the pre-cancerous condition, the non-cancerous condition, the bacterial infection, the bowel disorder or the infection associated with a cancer to be treated or diagnosed and the subject to be treated. Generally, however, the concentration of photosensitizer in the product is in the range of from about 1% to about 50%, from about 1% to about 40%, e.g. from about 2% to about 25%, or from about 5% to about 20% by weight of the total weight of the pharmaceutical product. For example, the concentration of photosensitizer in the product can be present at a concentration of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50% by weight of the total weight of the pharmaceutical product. In some embodiments, the concentration of photosensitizer in the product is present at a concentration of about 20% by total weight of the product.

A pharmaceutical product for use in the methods as disclosed herein can comprise at least one pharmaceutically acceptable carrier and/or excipient. The skilled artisan will be able to select suitable carriers and excipients based on, for example, the route of administration chosen and the cancer, the infection associated with cancer, or the non-cancerous condition to be treated or diagnosed. Representative examples of excipients and carriers that can be used in the pharmaceutical products include agar, alginic acid, ascorbic acid, amino acids, calcium salts (e.g. calcium hydrogen phosphate), ammonium salts (e.g. ammonium acetate), and materials that are suitable for sustained, controlled or delayed release as disclosed herein. Miglyol® oils, which are esters of saturated coconut and palm kernel oil-derived caprylic and capric fatty acids and glycerin or propylene glycol, are also contemplated for use in formulation of the product. These can, for example, be used when forming capsules containing the photosensitizing agent.

In some embodiments, the pharmaceutical product or formulation includes citric acid. The amount of citric acid can range from about 1% to about 10% (w/w) of the product, or any percentage in between. For example, the amount of citric acid in the pharmaceutical product or formulation can be about 1%, 2%, 3%, 4%, 5%, 6%, 7%, 8%, 9% or 10% (w/w). In some embodiments, the amount of citric acid in the pharmaceutical product or formulation is about 5% (w/w).

In some embodiments, a pharmaceutical product is provided, comprising: an active ingredient that is Form C as disclosed herein, at least one triglyceride and at least one emulsifier. Methods of diagnosing or treating a cancer, a pre-cancerous condition, a non-cancerous condition, a bacterial infection, a bowel disorder or an infection associated with a cancer in the lower gastrointestinal tract are also provided, the method comprising administration of the solid pharmaceutical product to a subject in need thereof.

In some embodiments, the product comprises optionally one or more mucoadhesives, optionally one or more pharmaceutically acceptable excipients, optionally one or more surface penetration agents and optionally one or more chelating agents. Such additional components are described infra.

In some embodiments, a pharmaceutical product is provided, comprising: a) an active ingredient that is Form C as disclosed herein, with 10% water, b) Prosolv®, c) HPMC E5, d) Kollidon VA 64, e) crospovidone, f) sodium stearyl fumarate, g) mannitol and h) Cab-O-Sil®. In some embodiments, the product is coated with at least one selected from the group of: Eudragit® S100, Eudragit® L100, TEC and talc. Methods of diagnosing or treating a cancer, a pre-cancerous condition, a non-cancerous condition, a bacterial infection, a bowel disorder or an infection associated with a cancer in the lower gastrointestinal tract are also provided, the method comprising administration of the solid pharmaceutical product to a subject in need thereof.

In some embodiments, the pharmaceutical product as disclosed herein is a solid pharmaceutical product.

In embodiments comprising a triglyceride, the triglyceride is comprised of one molecule glycerol and three fatty acid molecules. The three fatty acids can be identical or different fatty acids.

The triglycerides can be solid or liquid at room temperature, e.g. at temperatures of about 18° C. to about 25° C. Solid triglycerides are commonly denoted as fat, while liquid triglycerides are commonly denoted as oil. If solid triglycerides are used, the solid triglycerides can have a melting point of below or at the body temperature of a human or a non-human animal to which the solid pharmaceutical product is administered. In some embodiments, the solid pharmaceutical product is administered to a human, and the melting point of a solid triglyceride comprised in said pharmaceutical product is between about 26° C. and about 37° C.

The triglycerides can be synthetic, semi-synthetic or of animal and/or vegetable origin. The triglycerides can be pure/isolated triglycerides or a part of a mixture, such as a mixture of triglycerides, monoglycerides and/or diglycerides and/or free fatty acids and/or unsaponifiable lipids. Such mixtures are typically found in edible oils of animal and/or vegetable origin. If the triglycerides are part of a mixture, they can constitute the major part of said mixture. In the following, such mixtures are also referred to as "triglycerides."

In some embodiments, the at least one triglyceride is selected from the group of: edible oils of animal and/or vegetable origin and/or fractions thereof. For example, the at least one triglyceride can include soybean oil, palm oil, palm kernel oil, corn oil, olive oil, almond oil, safflower oil, peanut oil, coconut oil, sunflower oil, castor oil, pine oil, jojoba oil, cocoa butter, and palm olein, or mixtures thereof. Further examples of triglycerides include illipe butter, shea butter, cocoa butter, kokum butter, sal butter and other natural oils or fractions thereof. Other examples of triglycerides include hydrogenated or partially hydrogenated triglycerides selected from partially or fully hydrogenated soybean oil, rapeseed oil, cottonseed oil, sunflower oil, coconut oil and fractions thereof. The triglycerides can also be synthetic or semisynthetic triglycerides, such as medium-chain triglycerides (MCT).

In some embodiments, the triglyceride can be a triglyceride comprising glycerol and three identical or different $C_2$-$C_{22}$ fatty acids. In some embodiments, the triglyceride can comprise three identical or different $C_4$-$C_{18}$ fatty acids. In some embodiments, the triglyceride can comprise three identical or different $C_6$-$C_{18}$ fatty acids. In some embodiments, the triglyceride can comprise three identical or different $C_6$-$C_{12}$ fatty acids. In some embodiments, the triglyceride is a triglyceride comprising glycerol and three identical $C_2$-$C_{22}$ fatty acids. In some embodiments, the triglyceride can comprise three identical $C_4$-$C_{18}$ fatty acids. In some embodiments, the triglyceride can comprise three identical $C_6$-$C_{18}$ fatty acids. In some embodiments, the triglyceride can comprise three identical $C_6$-$C_{12}$ fatty acids.

In some embodiments, the solid triglyceride can be cocoa butter, tallow, hard fat, hydrogenated coco-glycerides, hydrogenated palm oil, tristearin, tripalmitin, trimyristin, and mixtures thereof. Such solid triglycerides can be used, particularly if the solid pharmaceutical product is a suppository. Suppository formulations containing such hard or solid fats are described supra.

The triglycerides can be prepared using standard processes and procedures well-known in the art, and are generally commercially available from various manufacturers such Sasol, Croda, Cognis, Gattefosse and others.

The emulsifier used in a solid pharmaceutical product as disclosed herein can be solid or liquid at room temperature, e.g. at temperatures of about 18° C. to about 25° C.

In some embodiments, the emulsifier is a non-ionic emulsifier. Exemplary non-ionic emulsifiers include, but are not limited to, short chain partial glycerides (i.e. esters of glycerol with short chain fatty acids, whereby only a part of the existing hydroxyl groups are esterified, e.g. mono- or diglycerides or mixtures of mono- and diglycerides), esters of glycerol with fatty acids and alpha-hydroxy acids, fatty alcohols and/or ethoxylated fatty alcohols, ethoxylated fatty acids, non-ethoxylated and ethoxylated esters of sorbitan and fatty acids, lecithins, polyethylene glycol based compounds, ethoxylated glycerides and poloxamers (i.e. triblock copolymers composed of a central hydrophobic chain of polyoxypropylene flanked by two hydrophilic chains of polyoxyethylene), Each exemplary non-ionic emulsifier is discussed in more detail infra.

Exemplary partial glycerides include, but are not limited to, mono- or diglycerides or mixtures of mono- and diglycerides of $C_6$-$C_{10}$ fatty acids.

Exemplary esters of glycerol with fatty acids and alpha-hydroxy acids include, for instance, glyceryl stearate citrate, glyceryl citrate/lactate/oleate/linoleate, glyceryl cocoate/citrate/lactate and glyceryl isostearate.

Exemplary fatty alcohols and/or ethoxylated fatty alcohols include, but are not limited to, cetostearyl alcohol or cetomacrogol.

Exemplary ethoxylated fatty acids include, but are not limited to, ethoxylated castor oil.

Exemplary non-ethoxylated and ethoxylated esters of sorbitan and fatty acids include, but are not limited to, products sold under brand names Span® and Tween®. These include, for example, polysorbates, (polyoxyethylene) sorbitan monolaurate, (polyoxyethylene) sorbitan monopalmitate, (polyoxyethylene) sorbitan monostearate, (polyoxyethylene) sorbitan monooleate, (polyoxyethylene) sorbitan tristearate and (polyoxyethylene) sorbitan trioleate.

Exemplary lecithins include, but are not limited to, egg yolk lecithin, soybean lecithin and phospholipids derived from lecithin (e.g. phosphatidylcholine).

Exemplary polyethylene glycol based compounds include, but are not limited to, polyethylene glycol 400 monostearate.

Exemplary ethoxylated glycerides include, but are not limited to, ethoxylated caprylocaproyl glyceride or products obtained from the reaction of polyethylene glycol and natural or hydrogenated oils, such as, for example, palm kernel oil, hydrogenated palm kernel oil, castor oil, hydrogenated castor oil, almond oil, apricot kernel oil and the like.

Other non-ionic emulsifiers include, but are not limited to, lauroyl macrogol-32 glyceride, Gelucire® 44/14 (Gattefosse); stearoyl macrogol glyceride, Gelucire® 50/13 (Gattefosse); PEG-50 castor oil, Emalex C-50 (Nihon Emulsion); Eumulgin® HRE 40 (Cognis); PEG-45 hydrogenated castor oil, PEG-8 caprylic/capric glycerides, Labrasol® (Gattefosse); either alone or in a mixture with other emulsifiers. In some embodiments, several Gelucires are mixed together, such as, for example, Gelucire® 44/14 with Gelucire® 50/02 (saturated polyglycolized glycerides) or Gelucire® 33/01 (glycerol esters of C8-C18 saturated fatty acids).

Exemplary poloxamers (i.e. triblock copolymers composed of a central hydrophobic chain of polyoxypropylene flanked by two hydrophilic chains of polyoxyethylene, also known by the trade name Pluronics®) include those which are liquid and have a pH below about 7 or about 6. These include, for example, Pluronic® L43, HLB 7-12 and Pluronic® L44, HLB 12-18, either alone or in a mixture with other emulsifiers, such as, for example, poloxamers such as Pluronic® F68.

The emulsifier can be present in the solid pharmaceutical product in an amount that will promote uniform distribution of the pharmaceutical product at the site of use, e.g. in the colon and rectum. A suitable amount of the emulsifier can be chosen in view of the amount of triglycerides present in the product. For example, the emulsifier can be present in a pharmaceutical product as disclosed herein in an amount ranging from about 0.5% to about 50%, about 1% to about 35%, or about 2% to about 30% by weight of the total weight of the solid pharmaceutical product. For example, the emulsifier can be present at a concentration of about 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49% or 50% by weight of the total weight of the solid pharmaceutical product.

The emulsifier or mixture of emulsifiers can be prepared using standard processes and procedures well-known in the art, although many are available commercially from various manufacturers such like Sasol, Croda, Cognis, Gattefosse, American Lecithin Company, BASF, Cytec and others.

A mucoadhesive encompasses a compound which exhibits an affinity for a mucosa surface, i.e. adheres to that surface through the formation of bonds which can be non-covalent in nature, whether binding occurs through interaction with the mucous and/or the underlying cells. The mucosa surface includes a mucosa surface of the lower gastrointestinal tract, in particular the mucosa of the colon and the rectum.

A mucoadhesive which is optionally present in a solid pharmaceutical product as disclosed herein can be one that is not degraded or metabolized by bacterial and non-bacterial enzymes present in the lower gastrointestinal tract, in particular in the colon and the rectum.

The mucoadhesive can be a natural or a synthetic compound, polyanionic, polycationic or neutral, water-soluble or water-insoluble. In some embodiments, the mucoadhesive is large and has a molecular weight ranging from about 500 kDa to about 3000 kDa or from about 1000 kDa to about 2000 kDa. The mucoadhesive can also be water-insoluble cross-linked. For example, the mucoadhesive can contain from about 0.05% to about 2% cross-linker by weight of the total polymer, prior to any hydration, in a water-swellable polymer capable of forming hydrogen bonds. The mucoadhesive compound can have a mucoadhesive force greater than about 100, greater than 120, or greater than about 150, expressed as a percent relative to a standard in vitro, as assessed according to the method of Smart et al., 1984, J. Pharm. Pharmacol., 36, pp. 295-299, which is incorporated herein by reference in its entirety.

Exemplary mucoadhesives can be selected from polysaccharides, such as, for example, dextran, pectin, amylopectin or agar; gums (e.g. guar gum or locust bean gum), salts of alginic acid (e.g. sodium alginate or magnesium alginate); poly(acrylic acid), crosslinked or non-crosslinked copolymers of poly(acrylic acid) and derivatives of poly(acrylic acid) such as salts and esters (e.g. carbomer (carbopol)).

When present, the mucoadhesive can be provided in a concentration range of from about 0.05% to about 50%, or from about 0.1 to about 25%, or from about 0.2% to about 10% by weight of the total weight of the solid pharmaceutical product. For example, the mucoadhesive can be present at a concentration of about 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49% or 50% by weight of the total weight of the solid pharmaceutical product.

In embodiments comprising an additional excipient other than a triglyceride or an emulsifier, the excipient can be at least one selected from the group of: an antiadherent, a filler, a binder, a flavor, a color, an odor enhancer, a glidant, a lubricant, a disintegrant, a solvent and a preservative. The skilled artisan will be able to select suitable excipients based on, for example, the route of administration chosen.

In embodiments in which a solid pharmaceutical product as disclosed herein optionally comprises one or more pharmaceutically acceptable solvents, such solvents can be a free fatty acid, a free fatty alcohol, an aqueous solution (e.g. a buffer), or water. In some embodiments, the solid pharmaceutical product does not contain any water, i.e. is water-free. By water-free, it is meant that no water is added to the solid pharmaceutical product and that any measurable water content of the product is due to water possibly contained in a photosensitizer agent, a triglyceride, an emulsifier, a mucoadhesive, a pharmaceutically acceptable excipient other than a triglyceride or an emulsifier, a surface penetration agent or a chelating agent that may be a component of the product.

Penetration enhancers can enhance the photosensitizing effect of the photosensitizer present in the pharmaceutical products of the invention. Surface penetration assisting agents such as, for example, dialkylsulphoxides (e.g. dimethylsulphoxide, or DMSO) can therefore be included in the products. The surface penetration assisting agent can be any of the skin penetration assisting agents described in the pharmaceutical literature, e.g. chelators (e.g. EDTA), surfactants (e.g. sodium dodecyl sulfate), non-surfactants, bile salts (sodium deoxycholate) and fatty acids (e.g. oleic acid). Examples of appropriate surface penetration assisting agents include isopropanol, HPE-101 (available from Hisamitsu), DMSO and other dialkylsulphoxides, in particular n-decylmethyl sulphoxide (NDMS), dimethylsulphacetamide, dimethylformamide (DMFA), dimethylacetamide, glycols, various pyrrolidone derivatives (Woodford et al., J. Toxicol. Cut. & Ocular Toxicology, 1986, 5: 167-177) and AZONE® (Stoughton et al., Drug Dpv. Ind. Pharm. 1983, 9: 725-744) or mixtures thereof. In some embodiments, the surface penetration assisting agents employed for use in a product, composition or formulation as herein described are those which are solid at ambient temperature.

In some embodiments, the solid pharmaceutical product does not contain a glycol (e.g. propylene glycol) as a surface penetration assisting agent.

The surface penetration agent can be provided in a concentration range of from about 0.2% to about 50%, from about 1% to about 40%, from about 2.5% to about 30%, from about 5% to about 25%, from about 7.5% to about 20%, or from about 10% to about 15% by weight of the total weight of the pharmaceutical product in which it is present. In some embodiments, the surface penetration agent is present in a concentration range of from about 0.5% to about 5% by weight of the total weight of the pharmaceutical product in which it is present. In some embodiments, the surface penetration agent is provided in a concentration range of about 0.2%, 0.5%, 1%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% by weight of the total weight of the pharmaceutical product in which it is present.

Chelating agents can also enhance the photosensitizing effect of the photosensitizer present in a pharmaceutical product as disclosed herein. Chelating agents can, for example, be included in order to enhance the accumulation of protoporphyrin (Pp) since the chelation of iron by the chelating agent prevents its incorporation into Pp to form heme by the action of the enzyme ferrochelatase, thereby leading to a buildup of Pp. By addition of a chelating agent, the photosensitizing effect can thereby be enhanced.

Suitable chelating agents that can be included in a composition, formulation or pharmaceutical product as disclosed herein include aminopolycarboxylic acids, or any of the chelants described in the literature for metal detoxification or for the chelation of paramagnetic metal ions in magnetic resonance imaging contrast agents. Exemplary chelating agents that are suitable for pharmaceutical use include, for example, EDTA, CDTA (cyclohexane triamine tetraacetic acid), DTPA and DOTA as well as well known derivatives and analogues thereof. To achieve the iron-chelating effect, desferrioxamine and other siderophores can also be used, e.g. in conjunction with aminopolycarboxylic acid chelating agents such as EDTA.

In some embodiments, the chelating agent can also serve as a surface penetration assisting agent. For example, EDTA can act as both a chelating agent as well as a surface penetration assisting agent.

Where present, the chelating agent can be used at a concentration of from about 0.01% to about 20%, from about 0.05% to about 15%, from about 0.1% to about 10%, from about 0.2% to about 5%, or from about 0.5% to about 2.5% by weight based on the total weight of the composition, formulation or pharmaceutical product in which it is present. In some embodiments, the chelating agent is used at a concentration of from about 0.01% to about 12% by weight of the total weight of the product. In some embodiments, the chelating agent is used at a concentration of from about 0.1% to about 10% by weight of the total weight of the product. For example, the chelating agent can be used at a concentration of about 0.01%, 0.05%, 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, or 20% by weight of the total weight of the product in which it is present.

In some embodiments, a solid pharmaceutical product as disclosed herein is provided in the form of a capsule comprising one or more liquid triglycerides. In some embodiments, the one or more liquid triglycerides is selected from triglycerides of glycerol and three identical or different $C_2$-$C_{22}$ fatty acids. In some embodiments, the one or more liquid triglycerides is selected from triglycerides of glycerol and three identical or different $C_4$-$C_{18}$ fatty acids. In some embodiments, the one or more liquid triglycerides is selected from triglycerides of glycerol and three identical or different $C_6$-$C_{18}$ fatty acids. In some embodiments, the one or more liquid triglycerides is selected from triglycerides of glycerol and three identical or different $C_6$-$C_{12}$ fatty acids. In some embodiments, the one or more liquid triglycerides is selected from the group of: tricaprylin, tricaproin, triheptanoin, caprylic/capric triglyceride, caprylic/capric/linoleic triglyceride and caprylic/capric triglyceride. To prepare or fill the capsule, the one or more liquid triglycerides can be mixed with the active ingredient, together with the one or more emulsifiers and optionally with a mucoadhesive, an excipient other than a triglyceride or an emulsifier, a surface penetration agent and/or a chelating agent. In some embodiments, the one or more emulsifier is selected from the group of: a lecithin, a phosphatidylcholine, an ethoxylated glyceride, polyoxyethylene sorbitan monooleate, dioctyl sodium sulfosuccinate, sodium lauryl sulfate, a poloxamer and a product obtained from the reaction of polyethylene glycol with a natural or a hydrogenated oil.

In some embodiments, a solid pharmaceutical product as disclosed herein is provided in the form of a capsule comprising one or more solid triglycerides having a melting point of below or at the body temperature of a human or a non-human animal to which the capsule is administered. In some embodiments, the capsule is administered to a human, and the melting point of said one or more solid triglycerides is between about 26° C. and about 37° C. In some embodiments, the one or more solid triglyceride is selected from the group of: cocoa butter, tallow, a hard fat, a hydrogenated coco-glyceride, hydrogenated palm oil, tristearin, tripalmitin trimyristin, and a hydrogenated coco-glyceride optionally mixed with glyceryl ricinoleate (e.g. those marketed under the name WITEPSOL® and MASSA ESTARINUM®). In some embodiments, the hydrogenated coco-glyceride is one with a low hydroxyl value and a melting point between about 31° C. and about 38° C. Exemplary hydrogenated coco-glycerides having such characteristics include, but are not limited to, WITEPSOL® H 32, WITEPSOL® H 35, WITEPSOL® H 37 and MASSA ESTARINUM® 299. To prepare or fill the capsule, the one or more solid triglycerides can be melted, and the active ingredient is mixed with the melted triglycerides, together with the one or more emulsifiers and optionally with a mucoadhesive, an excipient other than a triglyceride or an emulsifier, a surface penetration agent and/or a chelating agent. In some embodiments, the one or more emulsifier is selected from the group of: a lecithin, a phosphatidylcholine, an ethoxylated glyceride, polyoxyethylene sorbitan monooleate, dioctyl sodium sulfosuccinate, sodium lauryl sulfate, a poloxamer and a product obtained from the reaction of polyethylene glycol with a natural or a hydrogenated oil.

In some embodiments, a solid pharmaceutical product as disclosed herein is provided in the form of a capsule comprising several triglycerides, wherein at least one triglyceride is a liquid and at least one triglyceride is a solid. For example, the product can comprise a solid triglyceride and a liquid triglyceride. In some embodiments, the at least one liquid triglyceride comprises glycerol and three identical or different $C_2$-$C_{22}$ fatty acids. In some embodiments, the at least one liquid triglyceride comprises a glycerol and three identical or different $C_4$-$C_{18}$ fatty acids. In some embodiments, the at least one liquid triglyceride comprises a glycerol and three identical or different $C_6$-$C_{18}$ fatty acids. In some embodiments, the at least one liquid triglyceride comprises a glycerol and three identical or different $C_6$-$C_{12}$ fatty acids. In some embodiments, the at least one liquid triglyceride is selected from the group of: tricaprylin, tricaproin, triheptanoin, caprylic/capric triglyceride and caprylic/capric/linoleic triglyceride. The at least one solid triglyceride can have a melting point of below or at the body temperature of a human or a non-human animal to which the capsule is administered. In some embodiments, the capsule is administered to a human and the melting point of said at least one solid triglyceride is between about 26° C. and about 37° C. In some embodiments, the one or more solid triglyceride is selected from the group of: cocoa butter, tallow, a hard fat, a hydrogenated coco-glyceride, hydrogenated palm oil, tristearin, tripalmitin trimyristin, and a hydrogenated coco-glyceride optionally mixed with glyceryl ricinoleate (e.g. those marketed under the name WITEPSOL® and MASSA ESTARINUM®). In some embodiments, the hydrogenated coco-glyceride is one with a low hydroxyl value and a melting point between about 31° C. and about 38° C. Exemplary hydrogenated coco-glycerides having such characteristics include, but are not limited to, WITEPSOL® H 32, WITEPSOL® H 35, WITEPSOL® H 37 and MASSA ESTARINUM® 299. To prepare or fill the capsule, the at least one solid triglyceride can be melted and mixed with the at least one liquid triglyceride, the active ingredient, the one or more emulsifiers and optionally with a mucoadhesive, an excipient other than a triglyceride or an emulsifier, a surface penetration agent and/or a chelating agent. In some embodiments, the one or more emulsifier is selected from the group of: a lecithin, a phosphatidylcholine, an ethoxylated glyceride, polyoxyethylene sorbitan monooleate, dioctyl sodium sulfosuccinate, sodium lauryl sulfate, a poloxamer and a product obtained from the reaction of polyethylene glycol with a natural or a hydrogenated oil, and an ethoxylated fatty alcohol.

In some embodiments, a solid pharmaceutical product as disclosed herein is provided in the form of a capsule comprising several triglycerides, wherein at least one triglyceride is a liquid and at least one triglyceride is a solid, and a non-ionic emulsifier. For example, the product can comprise a solid triglyceride and a liquid triglyceride. In some embodiments, the at least one liquid triglyceride comprises glycerol and three identical or different $C_2$-$C_{22}$ fatty acids. In some embodiments, the at least one liquid triglyceride comprises a glycerol and three identical or different $C_4$-$C_{18}$ fatty acids. In some embodiments, the at least one liquid triglyceride comprises a glycerol and three identical or different $C_6$-$C_{18}$ fatty acids. In some embodiments, the at least one liquid triglyceride comprises a glycerol and three identical or different $C_6$-$C_{12}$ fatty acids. In some embodiments, the at least one liquid triglyceride is selected from the group of: tricaprylin, tricaproin, triheptanoin, caprylic/capric triglyceride and caprylic/capric/linoleic triglyceride. In some embodiments, the non-ionic emulsifier is a poloxamer or a product obtained from the reaction of polyethylene glycol with a natural or a hydrogenated oil. In some embodiments, the non-ionic emulsifier is selected from the group of: PLURONIC® L43, PLURONIC® L44, lauroyl macrogol-32 glyceride, GELUCIRE® 44/14 (Gattefosse), stearoyl macrogol glyceride, and GELUCIRE® 50/13 (Gattefosse). To prepare or fill the capsule, the at least one solid triglyceride can be melted and mixed with the at least one liquid triglyceride, the active ingredient, the one or more emulsifiers and optionally with a mucoadhesive, an excipient other than a triglyceride or an emulsifier, a surface penetration agent and/or a chelating agent. In some embodiments, the at least one liquid triglyceride, the emulsifier and optional other compounds can be formed to pellets, mini-tablets or granules. Excipients known in the art to form such pellets, mini-tablets or granules can be added, such as viscosity enhancers or fillers. The so-formed pellets, mini-tablets or granules can then be filled into a capsule.

In embodiments for oral administration, a solid pharmaceutical product as disclosed herein can be provided in the form of powder, a granule, a tablet, a pellet, a capsule or a mini-tablet, said products comprising as the one or more triglycerides solid and/or liquid triglycerides. Tablets, powder, granules, pellets or mini-tablets can be prepared by any method known to those of skill in the art. For example, tablets and mini-tablets can be prepared by direct compression of the components of the solid pharmaceutical product or by compression after granulation.

Suppositories and pessaries for use in the methods as disclosed herein can be prepared by any method known to those of skill in the art, e.g. by direct compression of a composition comprising a photosensitizer as disclosed herein or by compression after granulation or by molding. For example, a suppository can be prepared by melting an at least one solid triglyceride, mixing the melted triglyceride with the other components of the suppository composition, and pouring the mixture into a casting mold where the composition cools and hardens. Such embodiments can be adapted for insertion into the uterus, vagina cervix, or rectum.

Suppositories and pessaries can be formulated using any of the excipients and carriers mentioned above, e.g. lactose, microcrystalline cellulose or crospovidone. In some embodiments, suppositories and pessaries comprising a photosensitizer are formulated to melt or dissolve in the body after being administered to a subject. In such embodiments, the suppository or pessary can be water-soluble and can be made from macrogols, propylene glycols, glycerol, gelatin or mixtures thereof. In some embodiments, the suppository or pessary can further contain a bioadhesive agent, for example a mucoadhesive agent, to promote adhesion and thus prolonged contract of the composition to the mucosa membranes, e.g. the vaginal epithelium.

In some embodiments, suppositories or pessaries can be formulated with a fat or fat-like compound. Fats and fat-like compounds include, for example, hard fat (e.g. glycerides of $C_{8-18}$ fatty acids), a mixture of hard fat and additives, fat, paraffin, glycerol and synthetic polymers. In some embodiments, the suppository or pessary is formulated with a hard fat, which contain mixtures of the triglyceride esters of higher fatty acids along with varying proportions of mono- and diglycerides. Exemplary hard fats include the range of products sold under the trade name WITEPSOL® 1 (e.g. WITEPSOL® S55, WITEPSOL® S58, WITEPSOL® H32, WITEPSOL® H35 and WITEPSOL® H37). Suppositories and pessaries formulated in this way can melt after administration to the body and thereby release the photosensitizer contained therein. Accordingly, in some embodiments, the suppository or pessary formulated with a hard fat has a melting point between about 30° C. to about 42° C. For example, the suppository or pessary formulated with hard fat can have a melting point of about 30° C., about 31° C., about 32° C., about 33° C., about 34° C., about 35° C., about 36° C., about 37° C., about 38° C., about 39° C., about 40° C., about 41° C., or about 42° C.

The pharmaceutical products can additionally include lubricating agents, wetting agents, preserving agents, flavoring agents and/or odor enhancers. The pharmaceutical products for use in the methods as disclosed herein can be formulated so as to provide quick, sustained or delayed release of the photosensitizer after administration to the patient by employing procedures that are well known in the art. In embodiments intended for oral administration in treating conditions in the lower gastrointestinal tract, the formulation can be a delayed release formulation.

In some embodiments, the pharmaceutical product does not, comprise a non-aqueous liquid which has a dielectric constant of less than about 80 at about 25° C. In some embodiments, the pharmaceutical product does not comprise a non-aqueous liquid selected from the group of: an alcohol, an ether, an ester, a poly(alkylene glycol), a phospholipid, DMSO, N-vinylpyrrolidone, N,N-dimethylacetamide and mixtures thereof.

The compositions or pharmaceutical products as disclosed herein can additionally comprise an anti-cancer agent. Accordingly, embodiments are directed to use of a photosensitizer which is Form C as disclosed herein, together with an anti-cancer agent in the manufacture of a pharmaceutical product for use in the treatment of cancer or an infection associated with cancer. In some embodiments, the pharmaceutical product is in the form of a solid.

Embodiments are also directed to a kit or pack containing a pharmaceutical product as disclosed herein, and separately an anti-cancer agent for simultaneous, separate or sequential use in a method of treating a cancer or an infection associated with a cancer in a subject.

The anti-cancer agent present in the pharmaceutical product and/or kit as disclosed herein can be an anti-neoplastic agent. Exemplary anti-neoplastic agents include, but are not limited to, alkaloids (e.g. incristine, vinblastine, vinorelbine, topotecan, teniposiode, paclitaxel, etoposide and docetaxel), alkylating agents (e.g. alkyl sulfonates such as busulfan), aziridines (e.g. carboquone, ethylenimines and methylmelamines), nitrogen mustards (e.g. chlorambucil, cyclophosphamide, estramustin, ifosfamide and melphalan), nitrosurea derivatives (e.g. carmustine and lomustine), antibiotics (e.g. mitomycins, doxorubicin, daunorubicin, epirubicin and bleomycins), antimetabolites (e.g. folic acid analogues and antagonists such as methotrexate and raltitrexed), purine analogues (e.g. 6-mercaptopurine), pyrimidine analogues (e.g. tegafur, gemcitabine, fluorouracil and cytarabine), cytokines, enzymes (e.g. L-asparginase, ranpirnase), immunomodulators (e.g. interferons, immunotoxins, monoclonal antibodies), taxanes, topoisomerase inhibitors, platinum complexes (e.g. carboplatin, oxaliplatin and cisplatin) and hormonal agents (e.g. androgens, estrogens, antiestrogens) and aromatase inhibitors. Other anti-neoplastic agents for use in a pharmaceutical product or kit as disclosed herein include imiquimod, irenotecan, leucovorin, levamisole, etopisde and hydroxyurea.

In some embodiments, the anti-cancer agent is at least one selected from the group of: 5-fluorouracil, imiquimod, cytokines, mitomycin C, epirubicin, irenotecan, oxalipatin, leucovorin, levamisole, doxorubicin, cisplatin, etoposide, doxirubicin, methotrexate, taxanes, topoisomerase inhibitors, hydroroxyurea and vinorelbine. In some embodiments, the anti-cancer agent is an antibiotic such as mitomycin. In some embodiments, the anti-cancer agent is a pyrimidine analogue such as 5-fluorouracil.

Components and Methods for Delayed or Sustained Release of Compositions and Formulations In some embodiments, for example, in formulations adapted for oral administration, delayed release of an active agent from the formulation is provided. This can be useful when an oral formulation is to be administered for the treatment or diagnosis of conditions in the lower gastrointestinal tract. Delayed (e.g. sustained) release can be achieved using any of the methods known and described in the art such as, for example, pH-dependent systems designed to release the photosensitizer in response to a change in pH as well as time-dependent (or timed-release) systems designed to release the photosensitizer after a pre-determined time. There are various known methods and systems for oral colonic delivery of pharmaceutically active ingredients. For example, an oral pharmaceutical product can comprise one or more pharmaceutical excipients that provide for controlled release of the active ingredient and/or by coating the oral pharmaceutical product with a coating that provides such a time controlled release.

Pressure-controlled systems utilize the increase in pressure of the luminal contents to effect release of the active ingredient. In some embodiments, the active ingredient is dispersed in a melted solid triglyceride (suppository base) which can melt at body temperature, together with one or more emulsifiers, and the mixture is cooled such that a solid pharmaceutical product is obtained. The solid pharmaceutical product can be coated with ethyl cellulose. After the product is swallowed, the temperature of body allows the suppository base to melt, which increases the volume within the coating such that a balloon is formed of ethyl cellulose filled with liquid. This balloon is capable of remaining intact in the small intestine but can rupture when exposed to the more intense contractions and luminal contents of higher viscosity encountered in the colon.

Time-controlled systems (pulsatile release systems) are based on the principle of delaying the time of drug release until the system transits from mouth to colon. Pulsatile release systems can be formulated to undergo a lag-time of a predetermined span of time of no release, followed by a rapid and complete release or a delayed release of the loaded drugs(s) or active agent. A lag-time of 5 hours can be sufficient since small intestine transit is about 3-4 hours; this transit time is relatively constant and is not typically affected by the nature of formulation administered. In some embodiments, an oral solid pharmaceutical product is coated with lipid barriers such as carnauba wax and/or beeswax along with surfactants such as, for example, polyoxyethylene sorbitan monooleate. When the product comes in contact with an aqueous medium, the coat can emulsify or erode after the lag-time depending on the thickness of coat. The lag time of this system is independent of the gastrointestinal motility, pH, enzyme and gastric residence time. In some embodiments, the phainiaceutical product (liquid or solid) is filled into an insoluble capsule body housing which is sealed with a plug of a swellable hydrogel. Upon contact with gastrointestinal fluid, the plug can swell and push itself out of the capsule after the lag-time, which is controlled by the position and the dimensions of the plug. The plug material can be made up of, for example, (i) swellable materials coated with an insoluble but permeable polymer, e.g. polymethacrylates; (ii) an erodible compressed polymer such as, for example, hydroxypropyl methylcellulose (HPMC), polyvinyl alcohol, and polyethylene oxide; or (iii) a congealed melted polymer such as, for example, glyceryl monooleate or an enzymatically controlled erodible polymer such as, for example, pectin. In some embodiments, the capsule is coated with an enteric coating.

Bacteria responsive delivery is based on enzymatic activity of bacteria in the lower gastrointestinal tract, especially in the colon, where the bacterial count is approximately 10 million times higher than that in the proximal gastrointestinal tract.

The active agent to be delivered to the colon can be formulated in a compound or matrix that is degraded by enzymes produced and secreted from colonic bacteria. In some embodiments, a solid pharmaceutical product as disclosed herein is coated with a naturally occurring polysaccharide, such as, for example, an amylose. In the glassy state, amylose has suitable film-forming properties and is resistant to degradation by pancreatic enzymes in the small intestines. In combination with water-insoluble polymers, which reduce swelling and release of the active ingredient from the hydrophilic amylose, e.g. ethylcellulose, a film coating can be applied to the solid pharmaceutical product formulated as a tablet, a pellet, a liquid, or as pellets or granules filled in capsules.

Other suitable materials for sustained, controlled or delayed release include, but are not limited to, carbomers, carbopols, cellulose compounds and derivatives (e.g. microcrystalline cellulose (MCC), methylcellulose, carboxylmethyl cellulose sodium (SMC), ethylcellulose, hydroxyethyl cellulose, hydroxypropylcellulose), starch compounds and derivatives (e.g. corn starch, croscaramellose, crospovidone, cyclodextrins such as beta-cyclodextrin, lactose such as anhydrous lactose or hydrous lactose, maltodextrin, mannitol), synthetic polymers (e.g. methacrylic acid copolymers), polyethylene glycol derivatives (e.g. polysorbate), povidone, sorbitan derivatives, talcum, wax, polyethylene glycol, poloxamer, medium-chain triglycerides, glycerides of $C_{8-18}$ fatty acids (e.g. hard fat), Miglyol® oils, Kollidon® materials, and mixtures thereof. Such materials can be present in the compositions and pharmaceutical formulations as disclosed herein anywhere from about 1% to about 50% (w/w). For example, such materials can be present in the composition or pharmaceutical formulation at a concentration of about 1%, 2%, 5%, 10%, 15%, 20%, 25%, 30%, 35%, 40%, 45% or 50% (w/w).

For the controlled release of an active ingredient of an oral solid pharmaceutical product as disclosed herein, a pH dependent system can be considered. The pH of the small intestine increases aborally, and pH sensitive pharmaceutically acceptable excipients and coatings with a dissolution threshold in the range of about pH 5 to about pH 8 can be suitable for pH-controlled release of drugs that are to be delivered to the lower intestinal tract, e.g. to the colon. The pH in the terminal ileum is about 1-2 pH units higher than that in the cecum, and pH sensitive pharmaceutically acceptable excipients and coatings can begin to destabilize and degrade in the region of the terminal ileum/cecum. In some embodiments, an oral solid pharmaceutical product is one in which coating degradation is desired to be avoided in the stomach, and the coating can be selected such that it degrades at a more neutral pH. For example, the coating can be selected for degradation at a pH of about 5, 5.5, 6, 6.5, 7, 7.5, 8, or any pH in between. In some embodiments, the coating can be selected for degradation in the range of about pH 5.5 to about pH 7.5, or any pH in between. In some embodiments, the coating degrades at about pH 6.5 or more. In some embodiments, the coating is selected for degradation at about pH 6.5. In some embodiments, the solid pharmaceutical product is coated with one or more enteric coatings.

In some embodiments, the coating is one which is enterosoluble and gastroresistant. Such coatings can render the tablet or capsule stable to stomach pH, thus, the tablet/capsule begins to release the active agent contained therein after entry into the intestinal system, e.g. the colon. Exemplary coating materials that can be used with a composition or formulation as disclosed herein include synthetic, semi-synthetic or synthetic polymers. For example, the coating material can be at least one selected from the group of: cellulose acetate, hydroxypropyl methylcellulose, hydroxypropyl methylcellulose phthalate, a copolymer of methacryclic acid and methacrylic ester, and polyvinylacetophthalate. Other suitable coatings include cellulose acetate phthalate (CAP), cellulose acetate trimellitate, ethylcellulose, dibutyl phthalate and diethyl phthalate, a pectin, a pectin salt, and a cross-linked polymer and copolymer. Examples of cross-linked polymers and co-polymers include, for example, 2-hydroxy-ethyl methacrylate crosslinked with divinylbenzene and N,N'-bis (beta-styrene sulphonyl-4,4'-diaminobenzene. In some embodiments, the enteric coating is comprised of anionic polymers of methacrylic acid and methacrylate (Eudragit®). The Eudragit® grades of polymer which are capable of sustained release are contemplated for use as coating materials. Eudragit® grades of polymer are based on copolymers of acrylate and methacrylates with quaternary ammonium groups as functional groups as well as ethylacrylate methylmethacrylate copolymers with a neutral ester group. Such polymers are insoluble and permeable and their release profiles can be altered by varying mixing ratios and/or coating thickness. Exemplary Eudragit® polymers include the Eudragit® S- and L-types. In some embodiments, the enteric coating comprises Eudragit® S100 or Eudragit® L100, triethyl citrate and talc.

In some embodiments, the coating can comprise one or more Eudragit® polymers (e.g. Eudragit® FS, Eudragit® L30 D55, Eudragit L100® etc.) at a concentration of from about 1% to about 25% (w/w). For example, the coating can comprise a Eudragit® polymer or a mixture of Eudragit® polymers at a concentration of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or about 25% (w/w). In some embodiments, the coating comprises a Eudragit® polymer or a mixture of Eudragit® polymers at a concentration of about 10% (w/w). In some embodiments, the coating comprises a Eudragit® polymer or a mixture of Eudragit® polymers at a concentration of about 12% (w/w).

In some embodiments, the coating can comprise triethyl citrate at a concentration of from about 0.1% to about 5% (w/w). For example, the coating can comprise triethyl citrate at a concentration of about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5% 4.6%, 4.7%, 4.8%, 4.9%, or 5.0%. In some embodiments, the coating comprises triethyl citrate at a concentration of about 1.0% (w/w).

In some embodiments, the coating can comprise talc at a concentration of from about 1% to about 5% (w/w). For example, the coating can comprise talc at a concentration of about 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5% 4.6%, 4.7%, 4.8%, 4.9%, or 5.0% (w/w). In some embodiments, the coating comprises about 2.33% (w/w) talc.

In some embodiments, the coating can further comprise a diluent or lubricant. Diluents or lubricants suitable for oral pharmaceutical products are known in the art, and the skilled artisan is able to select a suitable diluent or lubricant based on various handbooks, (e.g. D. E. Bugay and W. P. Findlay (Eds) *Pharmaceutical Excipients* (Marcel Dekker, New York, 1999), E-M Hoepfner, A. Reng and P. C. Schmidt (Eds) *Fiedler Encyclopedia of Excipients for Pharmaceuticals, Cosmetics and Related Areas* (Edition Cantor, Munich, 2002) and H. P. Fielder (Ed) *Lexikon der Hilfsstoffe fur Phannazie,*

*Kosmetik and angrenzende Gebiete* (Edition Cantor Aulendorf, 1989)). The coating can comprise a diluent or lubricant at a concentration of from about 0.1% to about 2% (w/w). For example, the coating can comprise a diluents or a lubricant at a concentration of about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9% or 2.0% (w/w). In some embodiments, the coating comprises a diluent or lubricant at a concentration of about 0.65% (w/w). In some embodiments, the diluents or lubricant is magnesium stearate.

In some embodiments, the solid pharmaceutical product is coated with a first and second enteric coating, wherein said first enteric coating material is selected from the group of: cellulose acetate, hydroxypropyl methylcellulose, polyvinyl acetophthalate, cellulose acetate phthalate (CAP), ethylcellulose, dibutyl phthalate and diethyl phthalate, wherein said second coating is comprised of anionic polymers of methacrylic acid and methacrylate.

Coatings can be prepared by mixing together components as a solution and spraying or coating the solid formulation with the solution. As an exemplary embodiment for preparing a coating comprising a Eudragit® polymer, a coating solution can be prepared by mixing water and alcohol and slowing adding one or more Eudragit® polymers (e.g. Eudragit® FS, Eudragit® L30 D55, Eudragit® L100, etc.) and triethyl citrate to produce a solution ("Solution A"). In a separate receptacle, alcohol, talc and magnesium stearate can be mixed together. Once the solid formulation is ready for coating, the alcohol, talc and magnesium stearate mixture can be added to Solution A, and the resulting mixture can be continuously stirred or mixed until applied to the solid formulation. The mixture can be applied to the solid formulation by, for example, spraying, and the mixture can be applied with suitable parameters up to about a 10%-20% weight gain. The alcohol and water are subsequently removed by a suitable drying process.

A solid formulation as disclosed herein (e.g. tablets, capsules and pellets) can include one or more additional components that prolong the release of the active agent. Such delayed release agents are known in the art and can include, for example, gums such as guar gum. The desired content of such components (e.g. gums) in the solid formulation can readily be determined by those skilled in the art and can, for example, be in the range of from about 10% to about 70%, from about 15% to about 65%, from about 20% to about 60%, from about 25% to about 55%, from about 30% to about 50%, or from about 35% to about 45% by weight. In some embodiments, the content of such components in the solid formulation can be about 50% by weight. In some embodiments, the delayed release agent in the composition as disclosed herein is a Gelucire composition. A Gelucire composition is an inert semi-solid waxy material which is amphiphilic in character and is available with varying physical characteristics. Such agents can be identified by their melting point/Hydrophile-Lipophile Balance (HLB) value. The melting point is expressed in degrees Celsius and the HLB value is a numerical scale extending from 0 to approximately 20. Lower HLB values are indicative of more lipophilic and hydrophobic substances, and higher values are indicative of more hydrophilic and lipophobic substances. Gelucire compositions are generally considered to be fatty acid esters of glycerol and polyethylene glycol (PEG) esters or polyglycolised glycerides. The family of Gelucire compositions is characterized by a wide range of melting points. For example, a Gelucire composition can have a melting point of from about 33° C. to about 64° C. or from about 35° C. to about 55° C. A Gelucire composition can have a variety of HLB values. For example, a Gelucire composition can have an HLB value ranging from about 1 to about 14 or from about 7 to about 14. For example, Gelucire 44/14 designates a melting point of approximately 44° C. and an HLB value of about 14. An appropriate choice of melting point/HLB value of a Gelucire or a mixture of Gelucire compositions can provide the desired delivery characteristics for sustained release and is within the skill of the artisan to select. In some embodiments, where a Gelucire composition is present in a composition as disclosed herein, the Gelucire composition is one selected from the group of: Gelucire 44/14, Gelucire 50/02, and a mixture thereof. In embodiments where a mixture of Gelucire compositions is present, the mixture can be present in a mixture ratio ranging from about 25:50 to 75:25 (w/w) of Gelucire 44/14 to Gelucire 50/02. In some embodiments, the mixture is present in a mixture ratio of about 50:50 (w/w) Gelucire 44/14 to Gelucire 50/02. In some embodiments, the mixture is present in a mixture ratio of about 75:25 (w/w) of Gelucire 44/14 and Gelucire 50/02.

In some embodiments, the composition or formulation as disclosed herein includes excipients which degrade at the target site of treatment or where diagnosis is to be performed (e.g. in the lower part of the gastrointestinal system). In this way, the active agent is delivered directly to the desired point of treatment or diagnosis. For example, the photosensitizing agent can be formulated with (e.g. embedded in) a matrix which degrades in the lower part of the gastrointestinal system. In some embodiments, the composition or formulation can be designed comprising enteric polymers that have a relatively high threshold pH for dissolution. Examples of suitable matrix-forming agents include carbohydrates, for example disaccharides, oligosaccharides and polysaccharides, and the like. Other suitable matrix materials include alginates, amylase, celluloses, xanthan gum, tragacanth gum, starch, pectins, dextran, cyclodextrins, lactose, maltose and chitosan, and the like.

It is desired to achieve a high and substantially homogeneous or uniform concentration of active ingredient in the lower part of the gastrointestinal system. Accordingly, formulations and methods of administration can be used to achieve not only the desired prolonged or delayed release of the photosensitizing agent, but also a high and substantially homogeneous or uniform) concentration of HAL in the lower part of the gastrointestinal system. When performing PDT or PDD, an objective is to cover the whole colon with the administered photosensitizing agent. By regulating the time and place of release of the active ingredient in the colon, and by choosing a suitable triglyceride/emulsifier combination, the desired uniform coverage can be achieved. Accordingly, in some embodiments, a dosage form or a dosage regime which comprises a plurality of individual doses (e.g. tablets, capsules or a mixture of pellets) is provided, wherein the dosage form or regime is capable of releasing the active component at different rates and/or at different time intervals following administration. The individual doses can be contained within a single dosage form; for example a plurality of pellets, tiny pills, granules or mini-tablets can be provided within a single tablet or capsule in which the individual pellets, pills, granules or mini-tablets are capable of providing different release profiles for the active photosensitizing agent. These are referred to as "multi-particulate systems." In some embodiments, the dosage can comprise one or more single dose forms (e.g. one or more tablets or capsules) intended for separate or simultaneous administration in which the individual single dose forms differ in their release profiles. For example, for treatment of a patient, two or more different doses (e.g. capsules or tablets) containing the photosensitizing agent can be administered in which the two or more different doses have different release profiles. For example, in embodiments in which three different capsules are administered to a subject, the beginning, middle and end of the colon can be targeted with the three different capsules. Due to the peristaltic movement of the colon, the different doses can travel further down the colon before releasing their content, thereby allowing a uniform "coating" of the colon wall. In embodiments in which the clinical dose comprises more than one unit dose, different unit doses can be administered at the same time or at different time intervals.

The different release profiles (whether from individual particulates, e.g. pellets, within a single dosage form or from a plurality of single dose forms) can be achieved by any of the means previously described, for example, by altering the nature and/or concentration of any release agent, by providing a suitable coating, etc. In embodiments in which a coating is used, the nature of the coating material, its thickness and/or the concentration of the components within the coating can be varied as required to obtain the desired delayed release. Where the same coating material is used to coat a plurality of pellets, tablets or capsules, delayed release can be achieved by progressively increasing the concentration of the coating agent used to coat the individual doses. When coated pellets or granules are filled into a capsule or compressed together with excipients to form a tablet, the formulation is considered a multi-particulate dosage form. In such dosage forms, the tablets or capsules containing coated pellets or granules can be further coated with a suitable enteric coating, which can be the same or different to that used for coating of the pellets and granules.

In some embodiments, a combination of rapid and slow release agents can be used to provide the desired release profile. A suitable dosage regime can, for example, comprise administration of a plurality of capsules or tablets containing different release agents. For example, capsules containing Miglyol can be administered for relatively rapid release of the photosensitizing agent, while capsules containing Gelucire can be administered for a slower (delayed) release. Administration of a combination of these capsules can therefore be used to provide a more thorough coating of the entire colon mucosa.

Accordingly, embodiments are directed to an oral therapeutic or diagnostic dose of an active agent (e.g. Form C as disclosed herein) which comprises a plurality of tablets or capsules or a mixture of pellets comprising components that are degraded in the lower part of the gastrointestinal system in which the individual tablets, capsules or pellets are degraded with kinetic profiles whereby to secure a high and homogenous distribution of the active agent in the lower part of the gastrointestinal system. In some embodiments, the total dose can comprise several types of pellets in which the pellets degrade with different kinetic profiles. In some embodiments, the total dose comprising several types of pellets can be packaged in a single capsule. The various kinetic degradation profiles of the pellets can prolong release of the active agent. In some embodiments, the total dose can comprise several single dose forms (e.g. more than one tablet or capsule) wherein the single dose forms have different kinetic degradation profiles.

The oral dose formulation as disclosed herein can be provided in a pack which comprises a plurality of individual doses having different release profiles. Accordingly, embodiments are directed to a pack comprising a plurality of individual oral dose formulations, each comprising a photosensitizer agent (e.g. Form C as disclosed herein) and each having a different kinetic release profile, is provided. In some embodiments, the individual doses can be color coded with different colors.

Other pharmaceutical product embodiments contemplated for use are described in, for example, International Patent Publication No. WO 2010/142456, which is incorporated herein by reference in its entirety.

Embodiments as disclosed herein are not prone to degradation and/or composition. Accordingly, in some embodiments, the pharmaceutical product can be stored, e.g. at room temperature and humidity, for at least about 6 months, for at least about 12 months, for at least about 24 months or more (e.g. up to about 36 months).

Routes of Administration

The pharmaceutical products as disclosed herein can be administered orally, topically or by insertion into the rectum. The selected route of administration will depend on a number of factors including the severity and nature of the cancer, pre-cancerous condition, non-cancerous condition, bacterial infection, fungal infection, viral infection, parasitic infection, prion infection, bowel disorder or infection associated with a cancer to be diagnosed, the location of thereof and the nature of the active ingredient.

In some embodiments, a pharmaceutical product as disclosed herein can be administered by any means, such as, for example, orally, topically, by injection (e.g. intravenous, intramuscular, intraperitoneal, subcutaneous), by inhalation, or by insertion into the vagina or rectum. The route of administration will depend on a number of factors including the severity and nature of the condition to be treated or diagnosed, the location of the afflicted body part and the nature of the photo sensitizer. In embodiments in which oral administration is selected, the pharmaceutical product can be in the form of a tablet or as powder, granules or pellets contained in a capsule (e.g. a tablet). In embodiments in which topical application is selected, the pharmaceutical product can be in the form of a suppository, a pessary, a cream, a lotion, an ointment, or an emulsion.

Photodynamic diagnosis (PDD) of a cancer, a pre-cancerous condition, a non-cancerous condition, an infection, or a bowel disorder in the lower part of the gastrointestinal system can be carried out by endoscopic examination of the lower gastrointestinal tract, e.g. the colon and the distal part of the small bowel with a camera on a flexible tube passed through the anus of a human or non-human animal subject undergoing the endoscopic examination. Apart from diagnosis, endoscopic examination of the region also provides the opportunity for biopsy or removal of suspected lesions or polyps.

In some embodiments, it may be desirable for the colon to be free of solid matter for the PDD to be performed properly. In some embodiments, for one to three days, the subject to undergo PDD can be advised to follow a low fiber or clear-fluid only diet. The day prior to PDD, the bowels can be cleaned out ("bowel preparation" or "bowel prep"). Various bowel prep agents are available in solution or in tablet from. Bowel prep tablets contain compounds such as, for example, bisacodyl, and bowel prep solutions contain compounds such as, for example, L-sugars, sodium phosphate or polyethylene glycol and electrolytes. In an exemplary regime for a colonoscopy, the amount of bowel prep solution to be ingested is about 4 liters.

On the day of the PDD, a pharmaceutical product as disclosed herein can be ingested according to a prescribed dosage regime, e.g. in single dose of one unit or a single dose of several units or in multiple doses. In some embodiments, the pharmaceutical product is a solid. In some embodiments, the product is ingested between about 4 to about 12 hours prior to endoscopic examination. In some embodiments, the subject to which the product is administered is allowed to drink fluid. In embodiments in which the product is a suppository, the suppository can be placed at the site of examination. In embodiments in which an examination of the whole lower gastrointestinal tract is carried out, the suppository can be placed at the distal colon, e.g. cecum.

In addition, on the day of the PDD, a purgative or bowel preparation can be administered to the subject between about 30 minutes to 2 hours prior to administration of the oral solid pharmaceutical product on the day of the PDD. Suitable purgatives or bowel preparations are disclosed supra.

In some embodiments and to facilitate distribution of the active ingredient in the pharmaceutical product to the entire lower gastrointestinal tract, the subject can be administered a "booster" of fluid. In some embodiments, the booster of fluid comprises a bowel prep solution. The amount of booster can range from between about 50 mL to about 750 mL. For example, the amount of booster can be about 50 mL, 75 mL, 100 mL, 150 mL, 200 mL, 250 mL, 275 mL, 300 mL, 325 mL, 350 mL 375 mL 400 mL 425 mL, 450 mL, 475 mL, 500 mL, 525 mL, 550 mL, 575 mL, 600 mL, 625 mL, 650 mL, 675 mL, 700 mL, 725 mL or about 750 mL. In some embodiments, the amount of booster is about 500 mL. In some embodiments, the amount of booster is about 250 mL. The booster can be ingested at about 15 min to about 90 min after the ingestion of the pharmaceutical product. In some embodiments, the booster can be ingested at about 30 min to about 60 min after the ingestion of the pharmaceutical product. For example, the booster can be ingested at about 15, 20, 25, 30, 35, 40, 45, 50, 55, 60, 65, 70, 75, 80, 85 or 90 minutes or in any intervening amount of time after the ingestion of the pharmaceutical product. In some embodiments, a second booster of fluid can be administered to the patient at about 120 min to about 150 min after the ingestion of the pharmaceutical product. For example, the second booster can be administered at about 120, 125, 130, 135, 140, 145 or 150 minutes or in any intervening amount of time after the ingestion of the pharmaceutical product. In some embodiments, the second booster of fluid is a bowel prep solution. The uniform distribution of the active ingredient can further be promoted by having the subject move or roll from one side to another, e.g. lying 10 min on the right side, rolling to the back and lying 10 min on the back, rolling to the left side and lying 10 min on the left side.

After administration of the pharmaceutical product containing the photosensitizer(s), the site to be treated or diagnosed can be exposed to light to achieve a desired photosensitizing effect. The time period between administration and endoscopic examination including photoactivation (i.e. exposure of the site of examination to light) will depend on the nature of the pharmaceutical product, its form and the nature of the active ingredient. It is desirable that the active ingredient within said pharmaceutical product is converted into a photosensitizer and achieves an effective tissue concentration at the site of the examination prior to photoactivation. The amount of time between administration of the product and subsequent exposure of the target tissue or organ to light can range from about 0.5 hour to about 24 hours, from about 1 hour to about 18 hours, from about 2 hours to about 12 hours, or from about 3 hours to about 6 hours. In some embodiments, the amount of time between administration of the product and exposure to light is from about 1 hour to about 3 hours.

In some embodiments, a photosensitizer is applied to the affected or target site followed by irradiation after a period of time. In some embodiments, this procedure can be repeated from about 1 time to about 3 times, at intervals ranging from about 1 day to about 30 days. For example, the procedure can be repeated from 1 to 3 times at an interval of about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days or about 30 days, In embodiments in which additional treatment is contemplated, an additional treatment can be performed several months later, for example about 2 months later, about 3 months later, about 4 months later, about 5 months later, about 6 months later, about 7 months later, about 8 months later, about 9 months later, about 10 months later, about 11 months later, or about 12 months later.

In some embodiments, the diagnostic methods described herein can also be performed during surgery in which the diagnostic agent is given to the patient and surgery is performed under blue light. The lesion or disease fluoresces under blue light can aid the surgeon in defining the "surgical border" and can facilitate a more selective resection of the diseased area (e.g. tumor) to be performed. The diagnostic methods can comprise use of the photosensitizing agents as disclosed herein.

For therapeutic (e.g. PDT) purposes, methods for irradiation of different areas of the body, e.g. by lamps or lasers are well known in the art (see for example Van den Bergh, *Chemistry in Britain*, May 1986 p. 430-439). The wavelength of light used for irradiation can be selected to achieve an efficacious photosensitizing effect. An effective light is light in the wavelength range of from about 300 nm to about 800 nm, or from about 400 nm to about 700 nm, where the penetration of the light is found to be relatively deep. For example, the light wavelength can be about 300 nm, about 325 nm, about 350 nm, about 375 nm, about 400 nm, about 425 nm, about 450 nm, about 475 nm, about 500 nm, about 525 nm, about 550 nm, about 575 nm, about 600 nm, about 625 nm, about 650 nm, about 675 nm, about 700 nm, about 725 nm, about 750 nm, about 775 nm, or about 800 nm. The irradiation can be applied at a dose level of from about 10 Joules/cm$^2$ to about 100 Joules/cm$^2$ with an intensity of from about 20 mW/cm$^2$ to about 200 mW/cm$^2$ when a laser is used or a dose of from about 10 J/cm$^2$ to about 100 J/cm$^2$ with an intensity of about 50 mW/cm$^2$ to about 150 mW/cm$^2$ when a lamp is applied. Irradiation can be performed for a duration of from about 5 minutes to about 30 minutes. For example, irradiation can be performed for a duration of about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, or about 30 minutes. In some embodiments, irradiation is performed for about 15 minutes. In some embodiments, a single irradiation is used. In some embodiments, a light split dose in which the light dose is delivered in a number of fractions is used. In embodiments when a light split dose is employed, the light dose can be delivered at intervals ranging from, for example, a few minutes to a few hours between irradiations. In some embodiments, multiple irradiations can be applied.

For diagnostic (e.g. PDD) use, the area can first be inspected using white light. Suspicious or affected areas can then exposed to blue light (e.g. light ranging at a wavelength of from about 380 nm to about 450 nm). For example, the affected areas can be exposed to blue light at a wavelength of about 400 nm, about 405 nm, about 410 nm, about 415 nm, about 420 nm, about 425 nm, about 430 nm, about 435 nm, about 440 nm, about 445 nm or about 450 nm. The irradiation can be applied at a dose level of from about 10 Joules/cm$^2$ to about 100 Joules/cm$^2$ with an intensity of from about 20 mW/cm$^2$ to about 200 mW/cm$^2$ when a laser is used or a dose of from about 10 J/cm$^2$ to about 100 J/cm$^2$ with an intensity of about 50 mW/cm$^2$ to about 150 mW/cm$^2$ when a lamp is applied. The emitted fluorescence (about 635 nm) can then used to selectively detect affected tissue. Suitable endoscopes, e.g. colonoscopies, include state-of-the-art colonoscopes which are adapted to allow emission of such blue light in addition to white light, e.g. by being equipped with an internal filter assembly which passes primarily blue light. For example, a foot pedal can allow convenient switching between white and blue light. The light source can be a laser or a lamp. To visualize fluorescence, the colonoscope can be equipped with an integrated filter which blocks most of the reflected blue light. A camera-like a modified color charge-coupled device (CCD) camera can be used to capture images of the lower gastrointestinal tract and a standard color monitor can be used to display images of the lower gastrointestinal tract. Irradiation can be performed for a duration of from about 5 minutes to about 30 minutes. For example, irradiation can be performed for a duration of about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, or about 30 minutes. In some embodiments, a single irradiation is used. In some embodiments, a light split dose in which the light dose is delivered in a number of fractions is used. In embodiments when a light split dose is employed, the light dose can be delivered at intervals ranging from, for example, a few minutes to a few hours between irradiations. In some embodiments, multiple irradiations can be applied. The area of examination can further be inspected by use of white light, e.g. before, during or after irradiation with blue light. Polyps, cancerous tissue or pre-cancerous lesions identified due to its fluorescence may be removed during irradiation or in white light.

The abnormalities and disorders which can be treated with the compositions and methods as disclosed herein include any malignant, pre-malignant and non-malignant abnormalities or disorders responsive to photodynamic therapy, e.g. tumors or other growths, skin disorders such as psoriasis or actinic keratoses, skin abrasions, viral warts, varicose veins, spider veins, and other diseases or infections, e.g. bacterial, viral, prion, parasitic or fungal infections, and the like. In some embodiments, methods and compositions as disclosed herein can be used in the treatment of diseases, disorders or abnormalities where discrete lesions are formed to which the compositions is directly applied. For example, lesions, including tumors and the like, can be treated with the compositions and methods as disclosed herein.

In some embodiments, the condition to be treated can be a cosmetic condition, such as, for example, acne, skin aging, unwanted hair growth, or sparse hair growth.

The internal and external body surfaces which can be treated include the skin and all other epithelial and serosal surfaces, including, for example, mucosa, the linings of organs, e.g. the respiratory, gastro-intestinal and genito-urinary tracts, and glands with ducts which empty onto such surfaces (e.g. liver, hair follicles with sebaceous glands, mammary glands, salivary glands and seminal vesicles). In addition to the skin, such surfaces include, for example, the lining of the vagina, the endometrium and the urothelium. Such surfaces can also include cavities formed in the body following excision of diseased or cancerous tissue, e.g. brain cavities following the excision of tumors such as gliomas. Exemplary surfaces include: (i) the skin and conjunctiva, (ii) the lining of the mouth, pharynx, esophagus, stomach and intestines as well as the lining of intestinal appendages, rectum, and anal canal, (iii) the lining of the nasal passages, nasal sinuses, nasopharynx, trachea, bronchi, and bronchioles, (iv) the lining of the ureters, urinary bladder, and urethra, (v) the lining of the vagina, uterine cervix, and uterus, (vi) the parietal and visceral pleura, (vii) the lining of the peritoneal and pelvic cavities, and the surface of the organs contained within those cavities, (viii) the dura mater and meninges, (ix) any tumors in solid tissues that can be made accessible to photoactivating light.

The methods and compositions as disclosed herein can be used to treat and/or diagnose a cancer, a pre-cancerous condition, a non-cancerous condition, a bacterial infection, a fungal infection, a viral infection, a parasitic infection, a prion infection, a bowel disorder or an infection associated with a cancer. A "pre-cancerous condition" encompasses a disease, syndrome, or finding that, if left untreated, can lead to cancer. It can be a generalized state associated with a significantly increased risk of cancer. For example, a pre-cancerous condition can manifest itself by extensive/abnormal proliferation of cells, such as, for example, hyperplasia and neoplasia. The term "infection associated with cancer" encompasses any infection that is positively correlated with the development of cancer. An example of such an infection is human papillomavirus (HPV) infections.

Cancers and infections associated with cancer that can be treated and/or diagnosed can be present in any part of the body (e.g. skin, mouth, throat, esophagus, stomach, intestines, rectum, anal canal, nasopharynx, trachea, bronchi, bronchioles, urethra, urinary bladder, kidney, bone, blood, brain, head and neck, breast, throat, testicle, liver, pancreas, thyroid, ovary, urethra, vagina, cervix, uterus etc). Accordingly, the methods and compositions as disclosed herein can be used in the treatment and diagnosis of cancer of the skin, mouth, throat, esophagus, stomach, intestines, anal canal, nasopharynx, trachea, bronchi, bronchioles, urethra, urinary bladder, kidney, bone, blood, brain, head and neck, breast, throat, testicle, liver, pancreas, thyroid, ovary, urethra, uterus, cervix, vagina, rectum and colon. In some embodiments, the methods and uses as disclosed herein are used for the treatment or diagnosis of cervical cancer and colon cancer.

In some embodiments, a method of treating or diagnosing a condition in the colon is provided, the method comprising administering an enterosoluble capsule containing a photosensitizing agent that is Form C as disclosed herein to the colon. In some embodiments, the condition in the colon is colon cancer.

In some embodiments, a method of treating or diagnosing a condition in a subject is provided, the method comprising administering a composition as disclosed herein to a subject in need thereof, wherein the condition is irritable bowel syndrome (IBS), colorectal cancer, stomach cancer, esophageal cancer, diverticular disease, infectious colitis, ulcerative colitis, Crohn's disease; ischemic colitis, radiation colitis, esophagitis, inflammatory bowel disease, small intestinal bacterial overgrowth, chronic pancreatitis, pancreatic insufficiency, hepatic encephalopathy, diarrhea, constipation, gastrointestinal motility disorders, gastroesophageal reflux disease (GERD), gastroparesis, chronic intestinal pseudo-obstruction (Ogilvie's syndrome), colonic pseudo-obstruction, functional heartburn, post-operative ileus, hypertrophic pyloric stenosis, dyspepsia (including functional dyspepsia or non-ulcer dyspepsia), gastrointestinal damage, anal fissure, achlorhydria, achalasia, hemorrhoids, intestinal polyps, gastrointestinal tract cancer, pancreatic cancer, prostatic cancer, gastrointestinal tract inflammation, a bacterial infection. In some embodiments, the bacterial infection is caused by one or more of: *B. cereus, E. coli, H. pylori, C. jejuni, Listeria, Salmonella*, and *Shigella*.

In some embodiments, a method of treating or diagnosing a condition in a subject is provided, the method comprising administering a composition as disclosed herein to a subject in need thereof, wherein the subject is suffering from or susceptible to a bowel disorder. Susceptible to a bowel disorder is meant to include subjects at risk of developing a bowel disorder infection, e.g., subjects suffering from one or more of an immune suppression, subjects that have been exposed to other subjects with a bacterial infection, physicians, nurses, subjects traveling to remote areas known to harbor bacteria that causes travelers' diarrhea, subjects who drink amounts of alcohol that damage the liver, subjects with a history of hepatic dysfunction, etc.

In some embodiments, a method of treating cervical cancer is provided, the method comprising administration of a suppository containing a photosensitizer that is a Form C as disclosed herein to the cervix. In a preferred embodiment, a method of treating pre-cancerous lesions and cervical cancer is provided, the method comprising administration of a semi-solid composition containing Form C as disclosed therein to the cervix.

In one embodiment, the present invention provides Form C in association with an irradiation device for insertion, for example, into the vagina of a human for providing photodynamic therapy using Form C, the device comprising: a housing adapted to be fully inserted and secured in the vagina, the housing enclosing an LED lamp system and a power source for powering the LED lamp system, wherein the device is independently operational while located in the vagina.

The device is adapted to be fully inserted and secured in the vagina and does not require connection to an external power supply or light source during operation. By "independently operable" is meant that the device can provide illumination for photodynamic therapy without concurrent connection to any external device. The device is hence fully self-contained and forms an enclosed unit including both the light source and the power supply required for photodynamic procedures. For delivering Form C to the cervix for the treatment of cervical disorders, one may preferably turn to the disclosures of US Publication 2012/03300219 for a description of suitable devices for delivery of Form C and subsequent photodynamic therapy. The disclosures of US Publication 2012/03300219 are incorporated herein by reference for this purpose.

In some embodiments, a method of treating pre-cancerous lesions, HPV infections and cancerous lesions on the vulva and the anus is provided, the method comprising administration of a semi-solid composition containing a photosensitizer that is a Form C as disclosed herein to the vulva or the anus. In one embodiment, the present invention provides Form C in association with an irradiation device for irradiation of the vulva or the anus for providing photodynamic therapy using Form C, said device being a portable, self-contained irradiation apparatus for photodynamic treatment of the vulva and/or the anus, the apparatus comprising: a treatment surface capable of conforming to the area of the vulva and/or anus to be treated, an illumination system for directing light onto a treatment area of the vulva and/or anus, and a power source for the illumination system; wherein the illumination system is arranged to provide light at fluence rates of 50 mW/cm$^2$ or below. For delivering Form C to the vulva or the anus for the treatment of pre-cancerous lesions, HPV infections and cancerous lesions on the vulva or the anus, one may preferably turn to the disclosures of International Patent Application No. PCT/EP2012/075824 for a description of suitable devices for delivery of Form C and subsequent photodynamic therapy. The disclosures of International Patent Application No. PCT/EP2012/075824 are incorporated herein by reference for this purpose.

The methods and compositions as disclosed herein can also be used to treat a non-cancerous condition. A "non-cancerous condition" includes, but is not limited to, disease conditions such as, for example, colitis, Crohn's disease, irritable bowel disease and other viral, bacterial, parasitic or fungal infections or inflammation located in the lower gastrointestinal tract.

Embodiments are also directed to the use of a photosensitizer that is new Form C as disclosed herein, in the manufacture of a pharmaceutical product for use in the photodynamic treatment or diagnosis e.g. of a cancer, a pre-cancerous condition, a non-cancerous condition, a bacterial infection, a fungal infection, a viral infection, a parasitic infection, a prion infection, a bowel disorder or an infection associated with a cancer, wherein said pharmaceutical product is in the form of a solid. In some embodiments, the product is for use in the photodynamic treatment or diagnosis of a cancerous or non-cancerous condition in the lower part of the gastrointestinal system or in the female reproductive system.

Embodiments are directed to the use of a photosensitizer that is a new Form C as disclosed herein, in the manufacture of a pharmaceutical product for use in the photodynamic diagnosis and/or treatment of a cancer in the lower part of the gastrointestinal system, wherein said pharmaceutical product is in the form of a solid.

Embodiments also relate to the use of a photosensitizer that is a new Form C as disclosed herein, in the manufacture of a pharmaceutical product for use in the photodynamic diagnosis and/or treatment of a non-cancerous condition in the lower part of the gastrointestinal system, wherein said pharmaceutical product is in the form of a solid.

Embodiments are also directed to the use of a photosensitizer that is a new Form C as disclosed herein, in the manufacture of a pharmaceutical product for use in the photodynamic diagnosis and/or treatment of a cancer in the female reproductive system (e.g. cervical cancer), wherein said pharmaceutical product is in the form of a solid.

Embodiments can also relate to the use of a photosensitizer that is a new Form C as disclosed herein, in the manufacture of a pharmaceutical product for use in the photodynamic diagnosis and/or treatment of a non-cancerous condition in the female reproductive system, wherein said pharmaceutical product is in the form of a solid.

Doses can range from about 25 mg to about 500 mg of pharmaceutical product per administration. For example, the amount of pharmaceutical product that can be administered to a subject in need thereof can be about 25, 30, 35, 40, 45, 50, 75, 100, 125, 150, 175, 200, 225, 250, 275, 300, 325, 350, 375, 400, 425, 450, 475 or 500 mg, or any number in between.

The therapeutic and diagnostic methods as disclosed herein can also be used in the form of a combined therapy. For example, a course of PDT performed in relation to a cancer, a pre-cancerous condition, a non-cancerous condition, a bacterial infection, a bowel disorder or an infection associated with a cancer using any of the methods as disclosed herein can be followed by a PDD method (e.g. to determine the extent to which PDT has been effective and/or to detect any re-occurrence of the condition).

Accordingly, methods of administering a combined therapy to a subject in need thereof are provided, the methods comprising: (i) conducting a photodynamic treatment of a cancer, a pre-cancerous condition, a non-cancerous condition, a bacterial infection, or an infection associated with a cancer in the lower part of the gastrointestinal system or in the female reproductive system of said subject; and (ii) conducting photodynamic diagnosis on said subject, wherein at least one of steps (i) and (ii) is performed following administration to said patient of a photosensitizer which is 5-ALA or a precursor or derivative thereof (e.g. an ALA ester). In some embodiments, the methods comprise steps (i) and (ii) being administered following administration of said photosensitizer.

Embodiments are also directed to a method of photodynamic treatment or diagnosis of a cancer, a pre-cancerous condition, a non-cancerous condition, a bacterial infection, a bowel disorder or an infection associated with a cancer in a subject in need thereof, said method comprising the steps of: (a) administering to said subject a pharmaceutical product comprising a photosensitizer as disclosed herein; (b) optionally waiting for a time period necessary for the photosensitizer to achieve an effective tissue concentration at the desired site; and (c) photoactivating the photosensitizer.

Embodiments also relate to a method of diagnosing a cancer, a pre-cancerous condition, a non-cancerous condition, a bacterial infection, a bowel disorder or an infection associated with a cancer in an animal, wherein said animal is pre-administered a pharmaceutical product comprising a photosensitizer as disclosed herein, said method comprising: (i) optionally waiting for a time period necessary for the photosensitizer to achieve an effective tissue concentration at the desired site; and (ii) photoactivating the photosensitizer.

EXAMPLES

It will be appreciated that the invention should not be construed to be limited to the example, which is now described; rather, the invention is construed to include any and all applications provided herein and all equivalent variations within the skill of the ordinary artisan.

Preparation of New Form C

A solution of hexyl 5-aminolevulinate hydrochloride in acetonitrile, 158 mg in 1 ml, was heated to 55° C. The solution was filtered through a 0.2 μm nylon filter into 5 ml of refluxing hexanes (67° C.). The refluxing solution was stirred at 200 rotations per minute. The volume was reduced, through evaporation, until solids were observed, approximately 1 minute. An additional 5 ml of refluxing hexanes were added and the slurry refluxed for approximately 5 minutes. Form C was harvested by vacuum filtration and dried under nitrogen at room temperature.

Form C was prepared by exposing a solid sample of hexyl 5-aminolevulinate hydrochloride to 80° C. for approximately 3 to 6 hours.

Form C was prepared by heating a solid sample of hexyl 5-aminolevulinate hydrochloride 10° C. above the melting point for about 1 minute, with subsequent rapid cooling until solidified.

The following techniques were used to characterize Form C that was produced.

Differential Scanning Calorimetry

Differential scanning calorimetry was performed using a TA Instruments Model Q2000. Temperature calibration was performed using NIST traceable indium metal. The sample was placed into an aluminum Tzero crimped pan, covered with a lid. The prepared sample was exposed to 80° C. for three hours. The weight was recorded. A weighed aluminum pan configured as the sample pan was placed on the reference side of the cell. The sample was heated using a heating rate of 10° C./min from 25° C. to 150° C. Reported values were rounded to the nearest 0.1° C. Alternatively, differential scanning calorimetry was performed using a Perkin Elmer model DSC 8500. The sample was placed into a crimped aluminum pan, covered with a lid and heated using a heating rate of 10° C./min from 20° C. to 110° C.

Hot Stage Microscopy

Hot stage microscopy was performed using a Linkam hot stage (model FTIR 600) mounted on a Leica DM LP microscope. Sample was observed using a 20× objective. Sample was placed on a coverslip, and a second coverslip was then placed over the sample. Each sample was visually observed as the stage was heated. The hot stage was calibrated using USP melting point standards.

Infrared Spectroscopy

Infrared spectra were acquired on a Magna-IR 560® Fourier transform infrared (FT-IR) spectrophotometer (Thermo Nicolet) equipped with an Ever-Glo mid/far IR source, potassium bromide beamsplitter, and a deuterated triglycine sulfate detector. Wavelength verification was performed using NIST SRM 1921b (polystyrene). A diffuse reflectance accessory (the Collector™ II, Thermo Spectra-Tech) was used for sampling. The sample was diluted to 20% w/w active to KBr, by mixing with dry powdered potassium bromide (KBr). The mixture was prepared in a 13 mm diameter cup and leveled with a glass slide. The packed sample was exposed to 80° C. for six hours. Each spectrum represents 256 co-added scans collected at a spectral resolution of 4 cm$^{-1}$. The background data set was acquired with a blank sample beam. An absorbance spectrum was obtained by taking the ratio of these two data sets against each other. A Log 1/R (R=reflectance) spectrum was obtained by taking a ratio of these two data sets against each other and then converting to Kubelka-Munk units.

IR peak position variabilities are given to within ±4 cm$^{-1}$, based on the observed sharpness of the peaks picked and acquisition of data using a 2 cm$^{-1}$ data point spacing (4 cm$^{-1}$ resolution).

Raman Spectroscopy

Raman spectra were acquired on a FT-Raman module interfaced to a Magna-IR 860® Fourier transform infrared spectrophotometer (Thermo Nicolet) equipped with an indium gallium arsenide detector. Wavelength verification was performed using sulfur and cyclohexane. Each sample was prepared for analysis by placing the sample into a glass tube and exposure to 80° C. Approximately 0.75 W of Nd:YVO$_4$ laser power (1064 nm excitation wavelength) was used to irradiate the sample. Each spectrum represents 256 co-added scans collected at a spectral resolution of 4 cm$^{-1}$.

Raman peak position variabilities are given to within ±4 cm$^{-1}$, based on the observed sharpness of the peaks picked and acquisition of data using a 2 cm$^{-1}$ data point spacing (4 cm$^{-1}$ resolution).

Solid State $^{13}$C Cross Polarization Magic Angle Spinning Nuclear Magnetic Resonance The solid-state $^{13}$C cross polarization magic angle spinning (CP/MAS) nuclear magnetic resonance spectrum was acquired on a Varian $^{UNITY}$INOVA-400 spectrometer (Larmor frequencies: $^{13}$C=100.543 MHz, $^{1}$H=399.787 MHz). The sample was packed into a 4 mm PENCIL type zirconia rotor and rotated at 12 kHz at the magic angle. The prepared sample was exposed to approximately 80° C. for three hours within the spectrometer. The spectrum was acquired at approximately 80° C. with phase modulated SPINAL-64 high power $^{1}$H decoupling during the acquisition time using a $^{1}$H pulse width of 2.6 µs (90°), a ramped amplitude cross polarization contact time of 5 ms, a 30 ms acquisition time, a 5 second delay between scans, a spectral width of 45 kHz with 2700 data points, and 400 co-added scans. Chemical shifts were rounded to the nearest 0.1 ppm and are accurate to within ±0.2 ppm.

X-Ray Powder Diffraction

X-ray powder diffraction patterns were collected using a PANalytical X'Pert PRO MPD diffractometer. The specimen was analyzed using Cu radiation produced using an Optix long fine-focus source. An elliptically graded multilayer mirror was used to focus the Cu Kα X-rays of the source through the specimen and onto the detector. The specimen was sandwiched between 3-micron thick films. The prepared sample was exposed to 80° C. for three hours. It was analyzed in transmission geometry, and rotated parallel to the diffraction vector to optimize orientation statistics. A beam-stop, short antiscatter extension, antiscatter knife edge, and helium purge were used to minimize the background generated by air scattering. Soller slits were used for the incident and diffracted beams to minimize axial divergence. Diffraction patterns were collected using a scanning position-sensitive detector (X'Celerator) located 240 mm from the specimen. Prior to the analysis a silicon specimen (NIST standard reference material 640d) was analyzed to verify the position of the silicon 111 peak.

Peaks within the range of up to about 30° 2θ were selected. Although peaks are labeled on diffraction patterns and listed in tables, for technical reasons, different rounding algorithms were used to round each peak to the nearest 0.01° 2θ. The location of the peaks along the x-axis (° 2θ) in both the figures and the tables were automatically determined using proprietary software PatternMatch™ 3.0.4 and rounded to two significant figures after the decimal point. Peak position variabilities are given to within ±0.2° 2θ based upon recommendations outlined in the USP discussion of variability in x-ray powder diffraction. For d-space listings, the wavelength used to calculate d-spacings was 1.541874 Å, a weighted average of the Cu-K$_{α1}$ and Cu-K$_{α2}$ wavelengths. Variability associated with d-spacing estimates was calculated from the USP recommendation, at each d-spacing, and provided in the respective data tables.

Characteristic data for new Form C was obtained with X-ray powder diffraction (XRPD), differential scanning calorimetry (DSC), hot stage microscopy, infrared spectroscopy (IR), Raman spectroscopy, and solid state $^{13}$C cross polarization magic angle spinning nuclear magnetic resonance spectroscopy. The new Form is a crystalline material that melts near 99° C. The X-ray powder diffraction pattern of the new Form displays sharp peaks indicative of a crystalline material. The particle morphology is observed as rays, lathe, and/or blades. The new Form is the thermodynamically stable form above 65° C. Conversion to the new Form above 65° C. is demonstrated by hot stage microscopy based on the observed change in crystal morphology. Differential scanning calorimetry shows an endotherm near 99° C. that is consistent with the solid to liquid transition of a melt.

TABLE 1

Observed Peaks for X-ray Powder Diffraction Pattern of the new Form C of Hexyl 5-Aminolevulinate Hydrochloride

| 2θ | d space (Å) | Intensity (%) |
|---|---|---|
| 2.96 ± 0.20 | 29.813 ± 2.157 | 30 |
| 5.95 ± 0.20 | 14.842 ± 0.515 | 4 |
| 9.08 ± 0.20 | 9.740 ± 0.219 | 10 |
| 11.65 ± 0.20 | 7.594 ± 0.132 | 2 |
| 17.10 ± 0.20 | 5.185 ± 0.061 | 34 |
| 17.64 ± 0.20 | 5.029 ± 0.057 | 70 |
| 17.99 ± 0.20 | 4.932 ± 0.055 | 18 |
| 18.24 ± 0.20 | 4.864 ± 0.053 | 34 |
| 19.29 ± 0.20 | 4.601 ± 0.048 | 74 |
| 19.52 ± 0.20 | 4.547 ± 0.047 | 32 |
| 20.11 ± 0.20 | 4.416 ± 0.044 | 30 |
| 21.30 ± 0.20 | 4.172 ± 0.039 | 10 |
| 21.83 ± 0.20 | 4.071 ± 0.037 | 43 |
| 22.73 ± 0.20 | 3.912 ± 0.034 | 7 |
| 23.42 ± 0.20 | 3.799 ± 0.032 | 5 |
| 24.94 ± 0.20 | 3.570 ± 0.028 | 100 |
| 25.29 ± 0.20 | 3.522 ± 0.028 | 61 |
| 26.01 ± 0.20 | 3.426 ± 0.026 | 17 |
| 27.18 ± 0.20 | 3.281 ± 0.024 | 25 |
| 27.51 ± 0.20 | 3.242 ± 0.023 | 9 |
| 28.20 ± 0.20 | 3.165 ± 0.022 | 4 |
| 28.41 ± 0.20 | 3.141 ± 0.022 | 5 |

TABLE 2

Prominent Peaks for X-ray Powder Diffraction Pattern of the new Form C of Hexyl 5-Aminolevulinate Hydrochloride

| 2θ | d space (Å) | Intensity (%) |
|---|---|---|
| 2.96 ± 0.20 | 29.813 ± 2.157 | 30 |
| 9.08 ± 0.20 | 9.740 ± 0.219 | 10 |
| 17.10 ± 0.20 | 5.185 ± 0.061 | 34 |
| 17.64 ± 0.20 | 5.029 ± 0.057 | 70 |
| 17.99 ± 0.20 | 4.932 ± 0.055 | 18 |
| 18.24 ± 0.20 | 4.864 ± 0.053 | 34 |
| 19.29 ± 0.20 | 4.601 ± 0.048 | 74 |
| 19.52 ± 0.20 | 4.547 ± 0.047 | 32 |
| 20.11 ± 0.20 | 4.416 ± 0.044 | 30 |
| 21.83 ± 0.20 | 4.071 ± 0.037 | 43 |
| 24.94 ± 0.20 | 3.570 ± 0.028 | 100 |
| 25.29 ± 0.20 | 3.522 ± 0.028 | 61 |
| 26.01 ± 0.20 | 3.426 ± 0.026 | 17 |
| 27.18 ± 0.20 | 3.281 ± 0.024 | 25 |

TABLE 3

Observed Peaks for Infrared Spectrum of the new Form C of Hexyl 5-Aminolevulinate Hydrochloride cm$^{-1}$

| |
|---|
| 3451 ± 4 |
| 2962 ± 4 |
| 2933 ± 4 |
| 2742 ± 4 |
| 2692 ± 4 |
| 2646 ± 4 |
| 2056 ± 4 |
| 1995 ± 4 |
| 1743 ± 4 |
| 1695 ± 4 |
| 1593 ± 4 |
| 1565 ± 4 |
| 1510 ± 4 |
| 1475 ± 4 |
| 1435 ± 4 |
| 1413 ± 4 |

TABLE 3-continued

Observed Peaks for Infrared Spectrum of the new
Form C of Hexyl 5-Aminolevulinate Hydrochloride
cm$^{-1}$

| |
|---|
| 1393 ± 4 |
| 1369 ± 4 |
| 1303 ± 4 |
| 1243 ± 4 |
| 1212 ± 4 |
| 1184 ± 4 |
| 1123 ± 4 |
| 1096 ± 4 |
| 1063 ± 4 |
| 1006 ± 4 |
| 984 ± 4 |
| 959 ± 4 |
| 900 ± 4 |
| 817 ± 4 |
| 797 ± 4 |
| 727 ± 4 |
| 651 ± 4 |
| 556 ± 4 |
| 447 ± 4 |

TABLE 4

Characteristic Peaks for Infrared Spectrum of the new
Form C of Hexyl 5-Aminolevulinate Hydrochloride
cm$^{-1}$

| |
|---|
| 2056 ± 4 |
| 1995 ± 4 |
| 1565 ± 4 |
| 1369 ± 4 |
| 1303 ± 4 |
| 1243 ± 4 |
| 1123 ± 4 |
| 651 ± 4 |

TABLE 5

Observed Peaks for Raman Spectrum of the new
Form C of Hexyl 5-Aminolevulinate Hydrochloride
cm$^{-1}$

| |
|---|
| 2989 ± 4 |
| 2934 ± 4 |
| 2874 ± 4 |
| 1734 ± 4 |
| 1558 ± 4 |
| 1439 ± 4 |
| 1417 ± 4 |
| 1395 ± 4 |
| 1304 ± 4 |
| 1246 ± 4 |
| 1125 ± 4 |
| 1081 ± 4 |
| 1006 ± 4 |
| 980 ± 4 |
| 890 ± 4 |
| 818 ± 4 |

TABLE 6

Characteristic Peaks for Raman Spectrum of the new
Form C of Hexyl 5-Aminolevulinate Hydrochloride
cm$^{-1}$

| |
|---|
| 1417 ± 4 |
| 1246 ± 4 |
| 1081 ± 4 |
| 980 ± 4 |

TABLE 7

Observed Chemical Shifts for Solid State $^{13}$C Cross Polarization
Magic Angle Spinning Nuclear Magnetic Resonance Spectrum of
the new Form C of Hexyl 5-Aminolevulinate Hydrochloride
ppm

| |
|---|
| 204.4 ± 0.2 |
| 202.8 ± 0.2 |
| 174.1 ± 0.2 |
| 173.2 ± 0.2 |
| 172.6 ± 0.2 |
| 65.2 ± 0.2 |
| 64.4 ± 0.2 |
| 48.7 ± 0.2 |
| 48.0 ± 0.2 |
| 36.0 ± 0.2 |
| 33.6 ± 0.2 |
| 32.7 ± 0.2 |
| 30.1 ± 0.2 |
| 29.7 ± 0.2 |
| 27.3 ± 0.2 |
| 26.7 ± 0.2 |
| 23.4 ± 0.2 |
| 14.8 ± 0.2 |
| 14.3 ± 0.2 |

Form C was prepared by exposing a solid sample of hexyl 5-aminolevulinate hydrochloride to 80° C. for approximately 3-5 hours under an inert atmosphere. Immediately after preparation, Form C was confirmed by differential scanning colorimetry (DSC) using a Perkin Elmer model DSC 8500.

Figure 11:
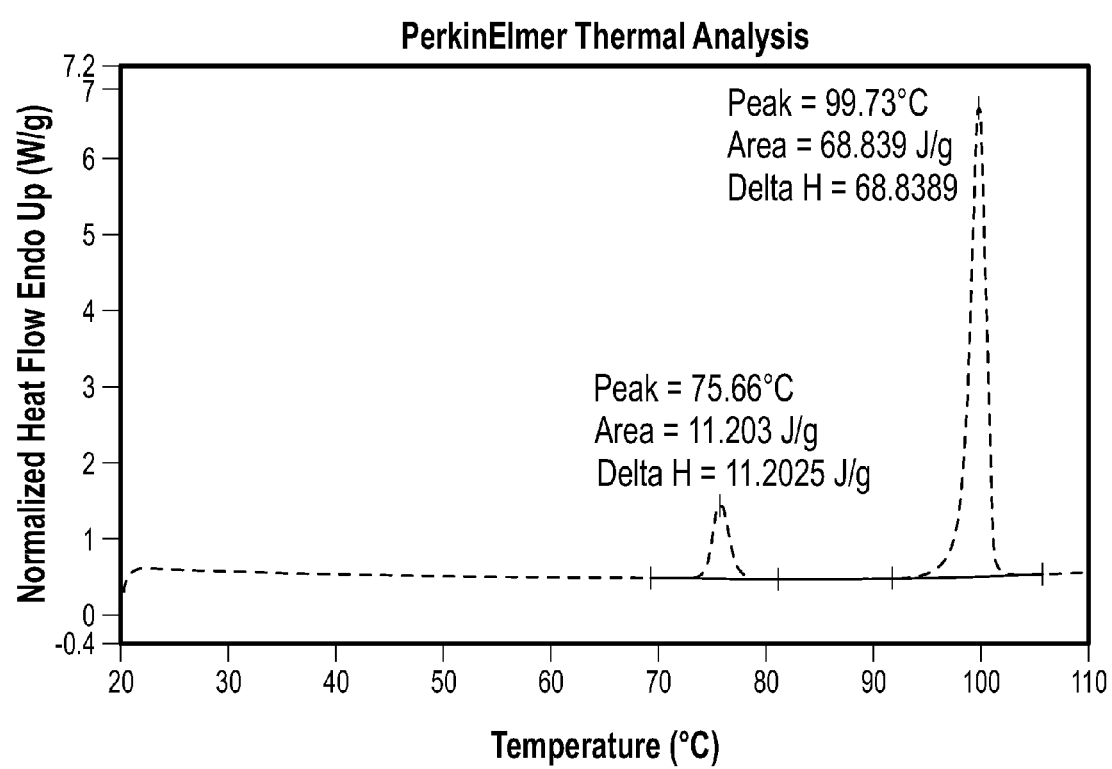
FIG. 11 is a differential scanning calorimetry (DSC) thermogram of hexyl 5-aminolevulinate hydrochloride.

The DSC thermogram of Form C (FIG. 10) shows an endothermic event at 101.5° C. which is attributed to the melting Form C. For comparison, the DSC thermogram of hexyl 5-aminolevulinate hydrochloride which was used for the synthesis of Form C as described above (FIG. 11) shows an endothermic event at 75.7° C. which is attributed to the phase transition from to Form C. The second endothermic event at 99.7° C. is attributed to the melting of Form C. The difference in peak melting point temperature for Form C between FIG. 10 and FIG. 11 is within the experimental variation expected for melting points determined as the peak temperature.

Incorporation by Reference

The contents of all references, patents, pending patent applications and published patents, cited throughout this application are hereby expressly incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

The invention claimed is:

1. A crystalline polymorph of hexyl-5-aminolevulinate hydrochloride (Form C), exhibiting an X-ray powder diffraction pattern comprising characteristic peaks expressed in degrees 2θ±0.20 at approximately 17.64, 19.29, 24.94, and 25.29.

2. The Form C polymorph of claim 1, exhibiting an X-ray powder diffraction pattern comprising characteristic peaks expressed in degrees 2θ±0.20 at approximately 2.96, 17.10, 17.64, 18.24, 19.29, 19.52, 20.11, 21.83, 24.94, and 25.29.

3. The Form C polymorph of claim 1, exhibiting an X-ray powder diffraction pattern comprising characteristic peaks expressed in degrees 2θ±0.20 at approximately 2.96, 9.08, 17.10, 17.64, 17.99, 18.24, 19.29, 19.52, 20.11, 21.83, 24.94, 25.29, 26.01 and 27.18.

4. The Form C polymorph of claim 1, having an X-ray powder diffraction pattern substantially the same as that shown in Table 1 or Table 2.

5. The Form C polymorph of claim 1, having infrared spectrum peaks substantially the same as that shown in Table 3 or Table 4.

6. The Form C polymorph of claim 1, having Raman spectrum peaks substantially the same as that shown in Table 5 or Table 6.

7. The Form C polymorph of claim 1, having solid-state carbon NMR shifts substantially the same as that shown in Table 7.

8. The Form C polymorph of claim 1, wherein the hexyl-5-aminolevulinate hydrochloride contains less than 5% by weight impurities.

9. The Form C polymorph of claim 1, wherein the hexyl-5-aminolevulinate hydrochloride is at least 95% pure.

10. The Form C polymorph of claim 1, wherein the hexyl-5-aminolevulinate hydrochloride is at least 98% pure.

11. A pharmaceutical composition comprising the Form C polymorph of claim 1 and a pharmaceutically acceptable carrier.

12. The pharmaceutical composition of claim 11, comprising one or more of: (i) at least one triglyceride, (ii) at least one emulsifier, (iii) one or more mucoadhesives, (iv) one or more surface penetration agents; and (v) one or more chelating agents.

13. The pharmaceutical composition of claim 12, wherein the composition comprises a suppository, a pessary, a suspension, an emulsion, a syrup, a sterile packaged powder, a cream, an ointment, or a lotion.

14. The pharmaceutical composition of claim 11, wherein the composition is substantially water-free.

15. The pharmaceutical composition of claim 11, wherein the composition is a capsule.

16. The pharmaceutical composition of claim 15, wherein the capsule is coated with at least one enteric coating.

17. A pharmaceutical composition comprising an effective amount of the Form C polymorph according to claim 1 effective in diagnosing and treating cancer of the uterus, cervix, vagina, rectum, colon, lower gastrointestinal tract, infection associated with cancer caused by human papilloma virus, non-cancerous lower gastrointestinal tract a human, inflammatory bowel disease, ulcerative colitis, Crohn's disease, inflammatory bowel syndrome, dysplasia of the female reproductive system, anus, penis, rosacea, and acne and a pharmaceutically acceptable carrier.

18. A method of conducting a photodynamic diagnosis (PDD) of a condition in a subject in need thereof, comprising administering the Form C polymorph of claim 1 to the subject.

19. A method of conducting a photodynamic therapy (PDT) of a condition in a subject in need thereof, comprising administering the Form C polymorph of claim 1 to the subject.

20. The method of claim 18 or 19, wherein the condition is one selected from the group of: a cancer, a pre-cancerous condition, a non-cancerous condition, a bacterial infection, a fungal infection, a viral infection, a parasitic infection, a prion infection, a bowel disorder and an infection associated with a cancer.

21. The method of claim 18 or 19, wherein the composition is administered topically, orally, intravenously, subcutaneously, intramuscularly, or intraperitoneally to the subject.

22. The method of claim 20, wherein the bacterial infection is caused by at least one selected from the group of: *Bacillus cereus, Campylobacter jejuni, Escherichia coli, H. pylori, Listeria* spp., *Salmonella*, and *Shigella*.

23. A method of detecting or treating a condition selected from cancer of the uterus, cervix, vagina, rectum, colon, lower gastrointestinal tract, infection associated with cancer caused by human papilloma virus, non-cancerous lower gastrointestinal tract a human, inflammatory bowel disease, ulcerative colitis, Crohn's disease, inflammatory bowel syndrome, dysplasia of the female reproductive system, anus, penis, rosacea, and acne in a human, comprising:
 (i) administering the pharmaceutical composition according to claim 11 to the subject;
 (ii) waiting for a period of time sufficient to allow the active ingredient to be converted to a photosensitizer and achieve an effective tissue concentration at a target site;
 (iii) photoactivating the photosensitizer; and
 (iv) detecting a fluorescent signal from the photosensitizer, wherein the presence of a fluorescent signal is indicative of the condition.

24. The Form C polymorph of claim 1 obtained by heating a solid sample of hexyl-5-aminolevulinate hydrochloride 10° C. above its melting point for about 1 minute.

25. The Form C polymorph of claim 1 obtained by exposing a solid sample of hexyl 5-aminolevulinate hydrochloride to 80° C. for approximately 3 to 6 hours.

* * * * *